United States Patent [19]

Belley et al.

[11] Patent Number: 5,428,033

[45] Date of Patent: Jun. 27, 1995

[54] SATURATED HYDROXYALKYLQUINOLINE ACIDS AS LEUKOTRIENE ANTAGONISTS

[75] Inventors: Michel L. Belley, Pierrefonds; Serge Leger, Dollard des Ormeaux; Patrick Roy; Yi B. Xiang, both of Pierrefonds; Marc Labelle, Ville d'Ile Perrot, all of Canada

[73] Assignee: Merck Frosst Canada, Inc., Kirkland, Canada

[21] Appl. No.: 774,396

[22] Filed: Oct. 10, 1991

Related U.S. Application Data

[63] Continuation-in-part of Ser. No. 596,844, Oct. 12, 1990, abandoned.

[51] Int. Cl.$^6$ ................. A61K 31/54; C07D 215/14
[52] U.S. Cl. ................. 514/228.2; 514/235.2; 514/255; 514/311; 514/313; 514/314; 544/62; 544/128; 544/363; 546/176
[58] Field of Search ............ 546/176; 544/62, 128, 544/363; 514/228.2, 235.2, 255, 311, 313, 314

[56] References Cited

U.S. PATENT DOCUMENTS

| | | | |
|---|---|---|---|
| 4,833,161 | 5/1989 | Wolff et al. | 514/445 |
| 4,851,409 | 7/1989 | Young et al. | 546/174 |
| 5,104,882 | 4/1992 | Young et al. | 514/311 |

FOREIGN PATENT DOCUMENTS

| | | |
|---|---|---|
| 0206751 | 12/1986 | European Pat. Off. |
| 0233763 | 8/1987 | European Pat. Off. |
| 0271287 | 6/1988 | European Pat. Off. |
| 0315399 | 5/1989 | European Pat. Off. |
| 0318093 | 5/1989 | European Pat. Off. |
| 0399818 | 5/1989 | European Pat. Off. |
| 0348155 | 12/1989 | European Pat. Off. |

Primary Examiner—C. Warren Ivy
Assistant Examiner—Raymond Covington
Attorney, Agent, or Firm—Mollie M. Yang; David L. Rose

[57] ABSTRACT

Compounds having the formula I:

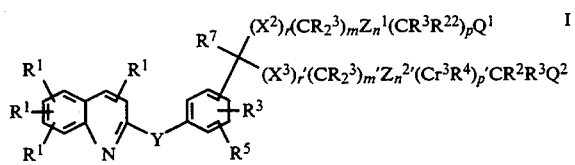

are leukotriene antagonists and inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection.

17 Claims, No Drawings

1

SATURATED HYDROXYALKYLQUINOLINE ACIDS AS LEUKOTRIENE ANTAGONISTS

CROSS-REFERENCE

This is a CIP of U.S. Ser. No. 596,844, Oct. 12, 1990, abandoned.

BACKGROUND OF THE INVENTION

The leukotrienes constitute a group of locally acting hormones, produced in living systems from arachidonic acid. The major leukotrienes are Leukotriene $B_4$ ($LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4(LTA_4)$, which is converted to the other leukotrienes by subsequent enzymatic steps. Further details of the biosynthesis as well as the metabolism of the leukotrienes are to be found in *Leukotrienes and Lipoxygenases*, ed. J. Rokach, Elsevier, Amsterdam (1989). The actions of the leukotrienes in living systems and their contribution to various diseases states are also discussed in the book by Rokach.

The art describes certain quinoline-containing compounds as having activity as antagonists of the actions of the leukotrienes. Thus, EP 318,093 (Merck) describes compounds of structure A. Structure B is disclosed in EP 315,399 (Rorer). Structure C is described in EP 348,155 (Rorer).

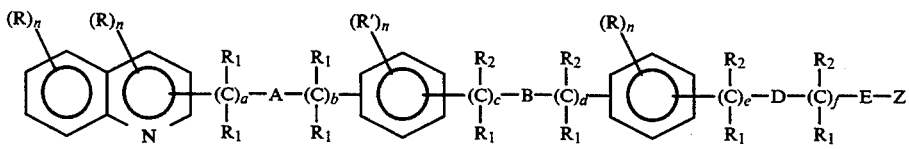

EP 318,093 (Merck)

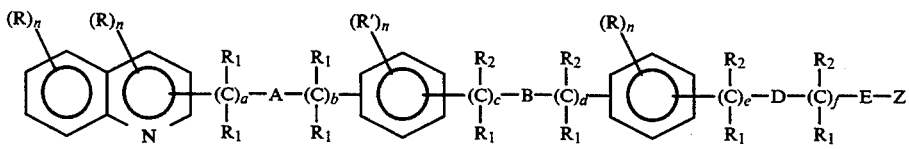

EP 315,399 (Rorer)

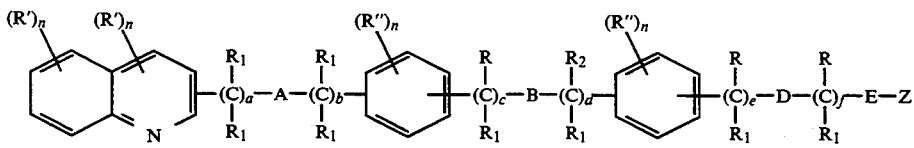

EP 348,155 (Rorer)

SUMMARY OF THE INVENTION

The present invention relates to saturated hydroxyalkyl quinoline acids having activity as leukotriene antagonists, to methods for their preparation, and to methods and pharmaceutical formulations for using these compounds in mammals (especially humans).

Because of their activity as leukotriene antagonists, the compounds of the present invention are useful as anti-asthmatic, anti-allergic, anti-inflammatory, and cytoprotective agents. They are useful in treating angina, cerebral spasm, glomerular nephritis, hepatitis, endotoxemia, uveitis, and allograft rejection.

DETAILED DESCRIPTION OF THE INVENTION

The compounds of this invention are best realized by Formula I:

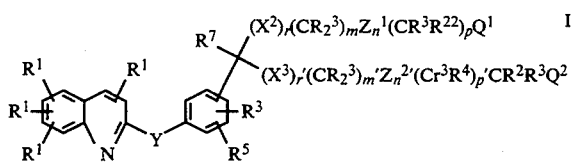

herein:

$R^1$ is H, halogen, $-CF_3$, $-CN$, $-N)_2$, or $N_3$;

$R^2$ is lower alkyl, lower alkenyl, lower alkynyl, $-F_3$, $-CH_2F$, $-CHF_2$, $CH_2CF_3$, substituted or unsubstituted phenyl, substituted or unsubstituted benzyl, substituted or unsubstituted 2-phenethyl, or two $R^2$ groups joined to the same carbon may form a ring of up to 8 members containing 0-2 heteroatoms chosen from O, S, and N;

$R^3$ is H or $R^2$;

$CR^3R^{22}$ may be the radical of a standard amino acid;

$R^4$ is halogen, $-NO_2$, $-CN$, $-OR^3$ $-SR^3$, $NR^3R^3$, $NR^3C(O)R^7$ or $R^3$;

$R^5$ is H halogen $-NO_2$ $-N_3$ $-CN$, $-SR^2$, $-NR^3R^3$, $-OR^3$, lower alkyl, or $-C(O)R^3$;

$R^6$ is $-(CH_2)_s-C(R^7R^7)-(CH_2)_s-R^8$ or $-CH_2-C(O)NR^{12}R^{12}$;

$R^7$ is H or $C_1-C_4$ alkyl;

$R^8$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or B) the radical W-R$^9$;

R$^9$ contains up to 20 carbon atoms and is (1) an alkyl group or (2) an alkylcarbonyl group of an organic acyclic or monocyclic carboxylic acid containing not more than 1 heteroatom in the ring;

R$^{10}$ is —SR$^{11}$, —OR$^{12}$ or —NR$^{12}$R$^{12}$;

R$^{11}$ is lower alkyl, —C(O)R$^{14}$, unsubstituted phenyl, or unsubstituted benzyl;

R$^{12}$ is H, R$^{11}$ or two R$^{12}$ groups joined to the same N may form a ring of 5 or 6 members containing 1–2 heteroatoms chosen from O, S, and N;

R$^{13}$ is lower alkyl, lower alkenyl, lower alkynyl, —CF$_3$, or substituted or unsubstituted phenyl, benzyl, or 2-phenethyl;

R$^{14}$ is H or R$^{13}$;

R$^{15}$ is R$^3$ or halogen;

R$^{16}$ is H, C$_1$–C$_4$ alkyl, or OH;

R$^{17}$ is lower alkyl, lower alkenyl, lower alkynyl, or substituted or unsubstituted phenyl, benzyl, or 2-phenethyl;

R$^{18}$ is lower alkyl, lower alkenyl, lower alkynyl, —CF$_3$, or substituted or unsubstituted phenyl, benzyl, or 2-phenethyl;

R$^{19}$ is lower alkyl, lower alkenyl, lower alkynyl, —CF$_3$, or substituted or unsubstituted phenyl, benzyl, or 2-phenethyl;

R$^{20}$ is H, C$_1$–C$_4$ alkyl, substituted or unsubstituted phenyl, benzyl, phenethyl, or pyridinyl or two R$^{20}$ groups joined to the same N may form a saturated ring of 5 or 6 members containing 1–2 heteroatoms chosen from O, S, and N;

R$^{21}$ is H or R17;

R$^{22}$ is R$^4$, CHR$^7$OR$^3$, or CHR$^7$SR$^2$;

m and m' are independently 0–8;

n and n' are independently 0 or 1, p and p' are independently 0–8;

m+n+p is 1–10 when r is 1 and X$^2$ is O, S, S(O), or S(O)$_2$;

m+n+p is 0–10 when r is 1 and X$^2$ is CR$^3$R$^{16}$;

m+n+p is 0–10 when r is 0;

m'+n'+p' is 0–10;

r and r' are independently 0 or 1;

s is 0–3;

Q$^1$ is —C(O)OR$^3$, 1H(or 2H)-tetrazol-5-yl, —C(O)OR$^6$, —C(O)NHS(O)$_2$R$^{13}$, —CN, —C(O)NR$^{12}$R$^{12}$, —NR$^{21}$S(O)$_2$R$^{13}$, —NR$^{12}$C(O)NR$^{12}$R$^{12}$, —NR$^{21}$C(O)R$^{18}$, —OC(O)NR$^{12}$R$^{12}$, —C(O)R$^{19}$, —S(O)R$^{18}$, —S(O)$_2$R$^{18}$, —S(O)$_2$NR$^{12}$R$^{12}$, —NO$_2$, —NR$^{21}$C(O)OR$^{17}$, —C(NR$^{12}$R$^{12}$)=NR$^{12}$, —C(R$^{13}$)=NOH; or if Q$^1$ is —C(O)OH and R$^{22}$ is —OH, —SH, —CHR$^7$OH or —NHR$^3$, then Q$^1$ and R$^{22}$ and the carbons through which they are attached may form a heterocyclic ring by loss of water;

Q$^2$ is OH or NR$^{20}$R$^{20}$;

W is O, S, or NR$^3$;

X$^2$ and X$^3$ are independently O, S, S(O), S(O)$_2$, or CR$^3$R$^{16}$;

Y is

—CR$^3$R$^3$—CR$^3$R$^3$—, or

-continued

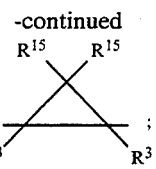

Z$^1$ and Z$^2$ are independently —HET(-R3-R5)—;

HET is the diradical of a benzene, a pyridine, a furan, or a thiophene; and the pharmaceutically acceptable salts thereof.

Definitions

The following abbreviations have the indicated meanings:

Et=ethyl
Me=methyl
Bz=benzyl
Ph=phenyl
t-Bu=tert-butyl
i-Pt=isopropyl
n-Pt=normal propyl
c-Hex=cyclohexyl
c-Pt=cyclopropyl
1,1-c-Bu=1,1-bis-cyclobutyl
1,1-c-Pt=1,1-bis-cyclopropyl (e.g., HOCH$_2$(1,1-c-Pr)CH$_2$CO$_2$Me is methyl 1-(hydroxymethoxy)cyclopropaneacetate)
c-=cyclo
Ac=acetyl
Tz=1H(or 2H)-tetrazol-5-yl
Th=2—or 3-thienyl
C$_3$H$_5$ =allyl
CHCH$_2$CH=1,2-cyclopropanediyl
c-Pen=cyclopentyl
c-Bu=cyclobutyl
phe=benzenediyl
pye=pyridinediyl
fur=furandiyl
thio=thiophenediyl
DEAD=diethyl azodicarboxylate
DHP=dihydropyran
DIAD=diisopropyl azodicarboxylate
r.t.=room temperature Alkyl, alkenyl, and alkynyl are intended to include linear, branched, and cyclic structures and combinations thereof.

"Alkyl" includes "lower alkyl" and extends to cover carbon fragments having up to 20 carbon atoms. Examples of alkyl groups include octyl, nonyl, norbornyl, undecyl, dodecyl, tridecyl, tetradecyl, pentadecyl, eicosyl, 3,7-diethyl-2,2-dimethyl-4-propylnonyl, 2-(cyclododecyl)ethyl, adamantyl, and the like.

"Lower alkyl" means alkyl groups of from 1 to 7 carbon atoms. Examples of lower alkyl groups include methyl, ethyl, propyl, isopropyl, butyl, sec-and tert-butyl, pentyl, hexyl, heptyl, cyclopropyl, cyclobutyl, cyclopentyl, cyclohexyl, cycloheptyl, 2-methylcyclopropyl, cyclopropylmethyl, and the like.

"Lower alkenyl" means alkenyl groups of 2 to 7 carbon atoms. Examples of lower alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2- methyl-2-butenyl, and the like.

"Lower alkynyl" means alkynyl groups of 2 to 7 carbon atoms. Examples of lower alkynyl groups include ethynyl, propargyl, 3-methyl-l-pentynyl, 2-heptynyl, and the like.

"Alkylcarbonyl" means alkylcarbonyl groups of 1 to 21 carbon atoms of a straight, branched or cyclic configuration. Examples of alkylcarbonyl groups are 2-methylbutanoyl, octadecanoyl, 11-cyclohexylundecanoyl and the like. Thus, the 11-cyclohexylundecanoyl group is c-Hex-$(CH_2)_{10}$—C(O)—.

Substituted phenyl, benzyl, 2-phenethyl and pyridinyl means structures with 1 or 2 substituents on the aromatic ring selected from lower alkyl, $R^{10}$, $NO_2$, $SCF_3$, halogen, —C(O)$R^7$, —C(O)$R^{10}$, CN, $CF_3$, and $CN_4H$.

Halogen means F, Cl, Br and I.

The prodrug esters of Q1 (i.e., when $Q^1$=—C(O)O$R^6$) are intended to mean the esters such as are described by Saari et al., J. Med. Chem., 21, No. 8, 746–753 (1978), Sakamoto et al., Chem. Pharm. Bull., 32, No. 6, 2241–2248 (1984) and Bundgaard et al., J. Med. Chem., 30, No. 3,451–454 (1987). Within the definition of $R^8$ some representative monocyclic or bicyclic heterocyclic radicals are:

2,5-dioxo-l-pyrrolidinyl,
(3-pyridinylcarbonyl)amino,
1,3-dihydro-l,3-dioxo-2H-isoindol-2-yl,
1,3-dihydro-2H-isoindol-2-yl,
2,4-imidazolinedion-l-yl,
2,6-piperidinedion-l-yl,
2-imidazolyl,
2-oxo-l,3-dioxolen-4-yl,
piperidin-1-yl,
morpholin-1-yl, and
piperazin-1-yl.

When $Q^1$ and $R^{22}$ and the carbons through which they are attached form a ring, the rings thus formed include lactones, lactams, and thiolactones.

It is intended that the definitions of any substituent (e.g., $R^1$ $R^2$ m, X etc.) in a particular molecule be independent of its definitions elsewhee in the molecule. Thus, —N$R^3R^3$ represents —NHH, —NHCH$_3$, —NHC$_6H_5$, etc.

The heterocycles formed when two $R^3$, $R^{12}$, or $R^{20}$ groups join through N include pyrrolidine, piperidine, morpholine, thiamorpholine, piperazine, and N-methylpiperazine.

"Standard amino acids", the radical of which may be $CR^3R^{22}$, means the following amino acids: alanine, asparagine, aspattic acid, arginine, cysteine, glutamic acid, glutamine, glycine, histidine, isoleucine, leucine, lysine, methionine, phenylalanine, proline, serine, threonine, tryptophan, tyrosine, and valine. (See F.H.C. Crick, Symposium of the Society of Experimental Biology, 12, 140 (1958)).

Some of the compounds described herein contain one or more centers of asymmetry and may thus give rise to diastereoisomers and optical isomers. The present invention is meant to comprehend such possible diastereoisomers as well as their racemic and resolved, optically active forms. Optically active (R) and (S) isomers may be resolved using conventional techniques.

Some of the compounds described herein contain olefinic double bonds, and unless specified otherwise, are meant to include both E and Z geometric isomers.

Preferred compounds of Formula I are those wherein:

$R^1$ is H, halogen, $CF_3$, or —CN;
$R^2$ is $C_1$–$C_4$ alkyl, —$CF_3$, —$CHF_2$, —$CH_2F$, or two $R^2$ groups joined to the same carbon may form a ring of up to 6 carbons;
$R^3$ is H or $R^2$;
$CR^3R^{22}$ may be the radical of a standard amino acid;
$R^4$ is —O$R^3$, —S$R^3$, N$R^3R^3$, NHC(O)CH$_3$, or $R^3$;
$R^5$ is H or halogen;
$R^6$ is —$(CH_2)_s$—C($R^7R^7$)—$(CH_2)_s$—$R^8$ or —CH$_2$-C(O)N$R^{12}R^{12}$;
$R^7$ is H or $C_1$–$C_4$ alkyl;
$R^8$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical W-$R^9$;
$R^9$ contains up to 20 carbon atoms and is (1) an alkyl group or (2) an alkylcarbonyl group;
$R^{10}$ is —S$R^{11}$, —O$R^{12}$ or —N$R^{12}R^{12}$;
$R^{11}$ is lower alkyl, —C(O)$R^{14}$, unsubstituted phenyl, or unsubstituted benzyl;
$R^{12}$ is H, $R^{11}$ or two $R^{12}$ groups joined to the same N may form a ring of 5 or 6 members containing 1–2 heteroatoms chosen from O, S, and N;
$R^{13}$ is lower alkyl, —$CF_3$, or substituted or unsubstituted phenyl, benzyl, or 2-phenethyl;
$R^{14}$ is H or $R^{13}$;
$R^{15}$ is $R^3$ or halogen;
$R^{16}$ is H, $C_1$–$C_4$ alkyl, or OH;
$R^{22}$ is $R^4$, —CH$_2$O$R^3$, or —CH$_2$S$R^2$;
m and m' are independently 0–4;
n and n' are independently 0 or 1;
p and p' are independently 0–4;
m+n+p is 1–9 when r is 1 and $X^2$ is O or S;
m+n+p is 0–9 when r is 1 and $X^2$ is $CR^3R^{16}$;
m+n+p is 0–9 when r is 0;
m'+n'+p' is 1–9,
r and r' are independently 0 or 1;
s is 0–3;
$Q^1$ is —C(O)O$R^3$, 1H(or 2H)-tetrazol-5-yl, -C(O)O$R^6$, —C(O)NHS(O)$_2R^{13}$, —C(O)N$R^{12}R^{12}$, —NHS(O)$_2R^{13}$; or if $Q^1$ is C(O)OH and $R^{22}$ is —OH, —SH, —CH$_2$OH or —NH$R^3$ then $Q^1$ and $R^{22}$ and the carbons through which they are attached may form a heterocyclic ring by loss of water;
$Q^2$ is OH;
W is O, S, or NH;
$X^2$ and $X^3$ are independently O, S, or $CR^3R^{16}$;
Y is

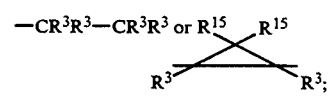

$Z^1$ and $Z^2$ are independently —HET(—$R^3$—$R^5$)—;
HET is the diradical of a benzene, pyridine, furan, or thiophene; and the pharmaceutically acceptable salts thereof.

Another group of preferred compounds are those wherein the $R^{22}$ α to $Q^1$ is lower alkyl, $CF_3$, or substituted or unsubstituted phenyl.

More preferred compounds of Formula I are represented by Formula Ia:

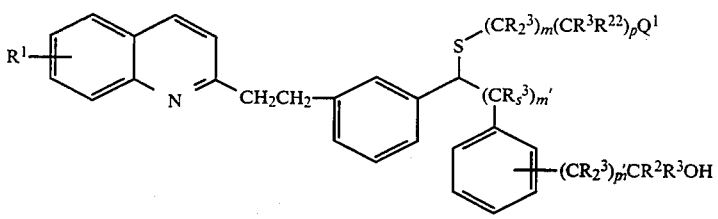

wherein:
R¹ is H, halogen, CN, or CF₃;
R²² is R³, —CH₂OR³, or —CH₂SR²;
Q¹ is —C(O)OH, 1H(or 2H)-tetrazol-5-yl, —C(O)NHS(O)₂R¹³, —C(O)NR¹²R¹², or —NHS(O)₂R¹³;
m' is 2 or 3;
p' is 0 or 1;
m+p is 1–5;
the remaining definitions are as in Formula I; and the pharmaceutically acceptable salts thereof.

Another group of more preferred compounds are as in Formula Ia, wherein:
m' is 0;
and the remaining definitions are as in Formula Ia.

The most preferred compounds of Formula Ia also have a lower alkyl on the carbon α to the group Q¹.

Another group of more preferred compounds of Formula I are represented by Formula Ib:

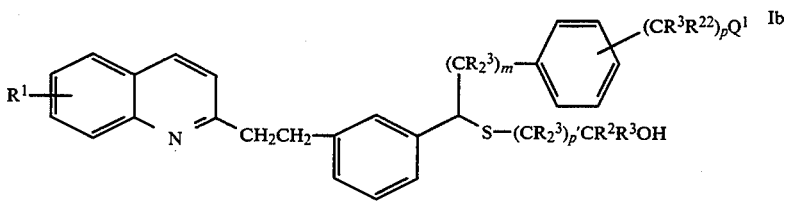

wherein:
R¹ is H, halogen, CN, or CF₃;
R²² is R³, —CH₂OR³, or —CH₂SR²;
Q¹ is —(O)OH, 1H(or 2H)-tetrazolyl, —(O)NHS(O)₂R¹³, —C(O)NR¹²R¹², or —NHS(O)₂R¹³;
m is 0, 2, or 3;
p is 0 or 1;
p' is 1–4;
m+p is 0–4;
the remaining definitions are as in Formula I; and the pharmaceutically acceptable salts thereof.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

It will be understood that in the discussion of methods of treatment which follows, references to the compounds of Formula I are meant to also include the pharmaceutically acceptable salts.

Utilities

The compounds of the present invention have modest activity as inhibitors of leukotriene biosynthesis, and are of utility principally because of their excellent activity as antagonists of the actions of the leukotrienes.

The ability of the compounds of Formula I to antagonize the actions of the leukotrienes makes them useful for preventing or reversing the symptoms induced by the leukotrienes in a human subject. This antagonism of the actions of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as psoriasis, atopic eczema, and the like, 6) cardiovarcular disorders such as angina, myocardial ischemia, hypertension, platelet aggregation and the like, 7) renal insufficiency arising from ischaemia induced by immunological or chemical (cyclosporin) etiology, 8) migraine or cluster headache, 9) ocular conditions such as uveitis, 10) heptaitis resulting from chemical, immunological or infections stimuli, 11) trauma or shock states such as burn injuries, endotoxemia and the like, 12) allograft rejection 13) prevention of side effects associated with therapeutic administration of cytokines such as Interleukin II and tumor mecrosis factor, 14) chronic lung diseases such as cystic fibrosis, bronchitis and other small and large-airway diseases, and 15) cholecystitis.

Thus, the compounds of the present invention may also be used to treat or prevent mammalian (especially, human) disease states such as erosive gartritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. The compounds also exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by Weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of compound I in suitable propellants, such as fluorocarbons or hydrocarbons.

Suitable topical formulations of Compound I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations with other drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the oxicams; and
(5) the biphenylcarboxylic acid derivatives; or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —$CH(CH_3)COOH$ or —$CH_2CH_2COOH$ group (which optionally can be in the form of a pharmaceutically acceptable salt group, e.g., —$CH(CH_3)COO^-Na^+$ or —$CH_2CH_2COO^-Na^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —$CH_2COOH$ group (which optionally can be in the form of a pharmaceutically acceptable salt group, e.g. —$CH_2COO^-Na^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

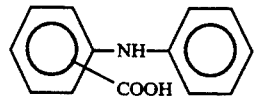

which can bear a variety of substituents and in which the free —COOH group can be in the form of a pharmaceutically acceptable salt group, e.g., —$COO^-Na^+$.

The biphenylcarboxylic acid derivatives which can be used comprise:diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

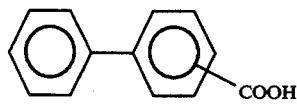

which can bear a variety of substituents and in which the free —COOH group can be in the form of a pharmaceutically acceptable salt group, e.g., —$COO^-Na^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non narcotic analgesics/non-steroidal anti-inflammatory drugs which have the general formula:

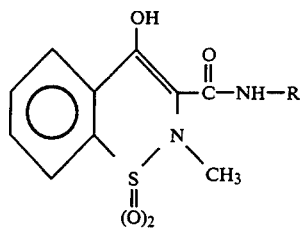

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid and ufenamate.

The following NSAIDs, designated by company code number (see e.g., *Pharmaprojects*), may also be used:

480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, LA2851, MR714, MR897, MY309, ON03144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDS are acetyl salicylic acid, diclofenac, fenbufen, fenoprofen, flurbiprofen, ibuprofen, ketoprofen, naproxen, phenylbutazone, piroxicam, sulindac and tolmetin.

Pharmaceutical compositions comprising the Formula I compounds may also contain inhibitors of the biosynthesis of the leukotrienes such as are disclosed in EP 138,481 (Apr. 24,1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982)

and 61,800 (Jun. 10, 1982); and in U.K. Patent Specification No. 2,058,785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as a-fluoromethyl-histidine, described in U.S. Pat. No. 4,325,961. The compounds of the Formula I may also be advantageously combined with an $H_1$ or $H_2$—receptor antagonist, such as for instance acetamazole, aminothiadiazoles disclosed in EP 40,696 (Dec. 2, 1981), benadryl, cimetidine, famotidine, framamine, histadyl, phenergan, ranitidine, terrenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxy-chromon-5-yloxy)-2-hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in Nature, Vol. 316, pages 126–131, 1985, and the like. Each of the references referred to in this paragraph is hereby incorporated herein by reference.

Other advantageous pharmaceutical compositions comprise the Formula I compounds in combination with anti-cholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylpred-nisolone, betamethasone, dexamethasone, beclomethasone, and the like.

Representative Compounds

Table I illustrates compounds representative of the present invention. Table II provides elemental analyses for compounds of Table I.

TABLE I

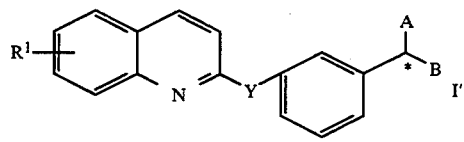

| EX. | * | $R^1$ | Y | A | B |
|---|---|---|---|---|---|
| 1 | RS | 7-Cl | $CHCH_2CH$ | $SCH_2CHMeCO_2H$ | $(CH_2)_2(1,2\text{-phe})CMe_2OH$ |
| 2 | RS | 7-Cl | $CH_2CH_2$ | $SCH_2CHMeCO_2H$ | $(CH_2)_2(1,2\text{-phe})(1\text{-c-Bu})OH$ |
| 3 | RS | 7-Cl | $CH_2CH_2CH$ | $SCH_2CHEtCO_2H$ | $(CH_2)_2(4\text{-Cl-1,2-phe})CMe_2OH$ |
| 4 | RS | 7-Cl | $CH_2CH_2$ | $SCH_2CHMeCO_2H$ | $(1,3\text{-phe})C_2OH$ |
| 5 | RS | 7-Cl | $CHCH_2CH$ | $S(CH_2)_2CMe_2OH$ | $(CH_2)_2(1,2\text{-phe})CO_2H$ |
| 6 | S | 7-Cl | $CH_2CH_2$ | $SCH_2(S)CHEtCO_2H$ | $(CH_2)_2(1,2\text{-phe})CMe_2OH$ |
| 7 | S | 7-Cl | $CH_2CH_2$ | $SCH_2(R)CH(NH_2)CO_2H$ | $(CH_2)_2(1,2\text{-phe})CMe_2OH$ |
| 8 | S | 7-Cl | $CH_2CH_2$ | $SCH_2(S)CHMeCO_2H$ | $(CH_2)_2(1,2\text{-phe})CMe_2OH$ |
| 9 | S | 7-Cl | $CH_2CH_2$ | $SCH_2(S)CH(n\text{-}Pr)CO_2H$ | $(CH_2)_2(1,2\text{-phe})CMe_2OH$ |
| 10 | RS | 7-Cl | $CH_2CH_2CH$ | $SCH_2CHEtCO_2H$ | $(CH_2)_2(1,2\text{-phe})CMe_2OH$ |
| 11 | RS | 7-Cl | $CHCBr_2CH$ | $SCH_2CHEtCO_2H$ | $(CH_2)_2(1,2\text{-phe})CMe_2OH$ |
| 12 | RS | 7-Cl | $CH_2CH_2$ | $SCH_2CMe_2CO_2H$ | $(CH_2)_2(1,2\text{-phe})CMe_2OH$ |
| 13 | RS | 7-Cl | $CH_2CH_2$ | $SCH_2CHMeCO_2H$ | $(CH_2)_2(1,2\text{-phe})CMe_2OH$ |
| 14 | RS | 7-Cl | $CH_2CH_2$ | $S(CH_2)_2CO_2H$ | $(CH_2)_2(1,2\text{-phe})CMe_2OH$ |
| 15 | RS | 7-Br | $CH_2CH_2$ | $SCH_2CHMeCO_2H$ | $(CH_2)_2(1,2\text{-phe})CMe_2OH$ |
| 16 | RS | 7-Cl | $CH_2CH_2$ | $S(CH_2)CMe_2OH$ | $(CH_2)_2(1,2\text{-phe})CHMeCO_2H$ |
| 17 | RS | 7-Cl | $CH_2CH_2$ | $SCH_2CHEtCO_2H$ | $S(CH_2)_2CMe_2OH$ |
| 18 | S | 7-Cl | $CH_2CH_2$ | $SCH_2CHMeCO_2H$ | $(CH_2)_2(1,2\text{-phe})C(CF_3)_2OH$ |
| 19 | RS | 7-Cl | $CHCH_2CH$ | $SCH_2CHEtCO_2H$ | $(CH_2)_2(1,3\text{-phe})CMe_2OH$ |
| 20 | RS | 7-Cl | $CHCH_2CH$ | $SCH_2CHEtCO_2H$ | $SCH_2CMe_2CMe_2OH$ |
| 21 | RS | 7-Cl | $CH_2CH_2$ | $S(CH_2)_2CMe_2OH$ | $(CH_2)_2(1,2\text{-phe})CO_2H$ |
| 22 | RS | 7-Cl | $CH_2CH_2$ | $S(CH_2)_2CMe_2OH$ | $(CH_2)_2(1,2\text{-phe})CONH_2$ |
| 23 | RS | 7-Cl | $CH_2CH_2$ | $SCH_2CHMeCO_2H$ | $SCH_2(1,2\text{-phe})CMe_2OH$ |
| 24 | RS | 7-$CF_3$ | $CH_2CH_2$ | $SCH_2CHMeCO_2H$ | $(CH_2)_2(1,4\text{-phe})CMe_2OH$ |
| 25 | RS | 7-Cl | $CH_2CH_2$ | $SCH_2CH(OMe)CO_2H$ | $(CH_2)_2(1,2\text{-phe})CMe_2OH$ |
| 26 | RS | 7-Cl | $CHCH_2CH$ | $SCH_2CHEtCO_2H$ | $(CH_2)_2(1,2\text{-phe})CH(CF_3)OH$ |
| 27 | RS | H | $CHCH_2CH$ | $SCH_2CHMeCO_2H$ | $(CH_2)_2(1,2\text{-phe})CMe_2OH$ |
| 28 | RS | H | $CH_2CH_2$ | $SCH_2CHEtCO_2H$ | $(CH_2)_2(1,2\text{-phe})CMe_2OH$ |
| 29 | RS | 7-Br | $CH_2CH_2$ | $SCH_2CHEtCO_2H$ | $(CH_2)_2(1,2\text{-phe})CMe_2OH$ |
| 30 | RS | 7-CN | $CH_2CH_2$ | $SCH_2CHEtCO_2H$ | $(CH_2)_2(1,2\text{-phe})CMeEtOH$ |
| 31 | RS | 7-Br | $CHCH_2CH$ | $SCH_2CHEtCO_2H$ | $(CH_2)_2(1,2\text{-phe})CEt_2OH$ |
| 32 | RS | 7-Cl | $CH_2CH_2$ | $SCH_2CHMeCO_2H$ | $(CH_2)_2(1,2\text{-phe})CMe_2NH_2$ |
| 33 | RS | 7-Cl | $CHCH_2CH$ | $SCH_2CHEtCO_2H$ | $(CH_2)_2(1,2\text{-phe})CHMeNHMe$ |
| 34 | RS | 7-Br | $CH_2CH_2$ | $SCH_2CHEtCO_2H$ | $(CH_2)_2(1,2\text{-phe})CHMeNMe_2$ |
| 35 | RS | 7-Cl | $CH_2CH_2$ | $SCH_2CHEtCO_2H$ | $(CH_2)_2(2,5\text{-fur})CMe_2OH$ |
| 36 | RS | 7-Cl | $CH_2CH_2$ | $SCH_2CHEtCO_2H$ | $(CH_2)_2(2,6\text{-pye})CMe_2OH$ |
| 37 | RS | 7-Cl | $CH_2CH_2$ | $SCH_2CHEtCO_2H$ | $(CH_2)_2(4,2\text{-pye})CMe_2OH$ |
| 38 | RS | 7-Cl | $CHCH_2CH$ | $SCH_2CHEtCO_2H$ | $(2,5\text{-thio})CMe_2OH$ |
| 39 | RS | 7-Cl | $CH_2CH_2$ | $SCH_2CHEtCO_2H$ | $(3,2\text{-pye})CMe_2OH$ |
| 40 | RS | 7-Br | $CH_2CH_2$ | $SCH_2CHEtCO_2H$ | $(1,4\text{-phe})CMe_2OH$ |
| 41 | RS | 7-Cl | $CH_2CH_2$ | $SCH_2CHMeCONHS(O)_2Me$ | $(CH_2)_2(1,2\text{-phe})CMe_2OH$ |
| 42 | RS | 7-Cl | $CH_2CH_2$ | $SCH_2CHMeCONH_2$ | $(CH_2)_2(1,2\text{-phe})CMe_2OH$ |
| 43 | RS | 7-Cl | $CH_2CH_2$ | $SCH_2CHMeTz$ | $(CH_2)_2(1,2\text{-phe})CMe_2OH$ |

TABLE I-continued

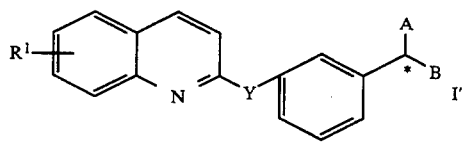

| EX. | * | R¹ | Y | A | B |
|---|---|---|---|---|---|
| 44 | RS | 7-Cl | CHCH₂CH | SCH₂CHEtTz | (CH₂)₂(1,2-phe)CMe₂OH |
| 45 | RS | 7-Cl | CHCH₂CH | SCH₂CHEtCONHS(O)₂CF₃ | (CH₂)₂(1,2-phe)CMe₂OH |
| 46 | RS | 7-Cl | CH₂CH₂ | SCH₂CHMeNO₂ | (CH₂)₂(7,2-phe)CMe₂OH |
| 47 | RS | 7-Cl | CH₂CH₂ | (CH₂)₂CONHS(O)₂Ph | (CH₂)₂(1,2-phe)CMe₂OH |
| 48 | RS | 7-Cl | CH₂CH₂ | SCH₂CHEtCO₂H | (CH₂)₂(1,2-phe)CH₂CMe₂OH |
| 49 | RS | 7-Cl | CHCH₂CH | SCH₂CHEtCO₂H | (CH₂)₃(1,2-phe)CMe₂OH |
| 50 | S | 7-Cl | CH₂CH₂ | SCH₂CH(CH₂CH=CH₂)CO₂H | (CH₂)₂(1,2-phe)CMe₂OH |
| 51 | S | 7-Cl | CHCH₂CH | SCH₂CHEtCO₂H | (CH₂)₂(1,2-phe)CHMeOH |
| 52 | S | 7-Cl | CH₂CH₂ | SCH₂CH(CH₂SMe)CO₂H | (CH₂)₂(1,2-phe)CMe₂OH |
| 53 | S | 7-Cl | CHCH₂CH | SCH₂CH(c-Pr)CO₂H | (CH₂)₂(1,2-phe)CMe₂OH |
| 54 | S | 7-Cl | CH₂CH₂ | CH₂CH(CH₂C≡CH)CO₂H | (CH₂)₂(1,2-phe)CMe₂OH |
| 55 | S | 7-Cl | CH₂CH₂ | SCH₂CHPhCO₂H | (CH₂)₂(1,2-phe)CMe₂OH |
| 56 | RS | 7-Cl | CH₂CH₂ | SCH₂CHEtCO₂H | (1,2-phe)CMe₂OH |
| 57 | RS | 7-Cl | CH₂CH₂ | S(CH₂)₂CMe₂OH | (1,3-phe)CO₂H |
| 58 | RS | 7-Cl | CH₂CH₂ | S(CH₂)₂CO₂H | CH₂CHOH(1,3-phe)CN4H |
| 59 | RS | 7-Cl | CH₂CH₂ | S(CH₂)₂CO₂H | CH₂CHOH(1,4-phe)CN4H |
| 60 | S | 7-Cl | CH₂CH₂ | S(CH₂)₂CO₂H | (CH₂)₂(1,2-phe)CMe₂OH |
| 61 | S | 7-Cl | CH₂CH₂ | SCH₂CHCF₃CO₂H | (CH₂)₂(1,2-phe)CMe₂OH |
| 62 | S | 7-Cl | CH₂CH₂ | S(CH₂)₃CO₂H | (CH₂)₂(1,2-phe)CMe₂OH |
| 63 | S | 7-Cl | CH₂CH₂ | S(CH₂)₂CHMeCO₂H | (CH₂)₂(1,2-phe)CMe₂OH |
| 64 | S | 7-Cl | CH₂CH₂ | S(O)₂CH₂(S)CHEtCO₂H | (CH₂)₂(1,2-phe)CMe₂OH |
| 65 | S | 7-Cl | CH₂CH₂ | SCH₂CH(CH₂OMe)CO₂H | (CH₂)₂(1,2-phe)CMe₂OH |
| 66 | S | 7-Cl | CH₂CH₂ | S(CH₂)₂CMe₂OH | (CH₂)₂(1,2-phe)CO₂H |
| 67 | R | 7-Cl | CH₂CH₂ | S(CH₂)₂CMe₂OH | (CH₂)₂(1,2-phe)CO₂H |
| 68 | S | 7-Cl | CH₂CH₂ | SCH₂(S)CHEtCO₂H | (CH₂)₂(1,3-phe)CMe₂OH |
| 69 | S | 7-Cl | CH₂CH₂ | SCH₂CHEtCO₂H | (CH₂)₂(7,3-phe)(1,1-c-Bu)OH |
| 70 | S | 7-Cl | CH₂CH₂ | S(CH₂)₂CMe₂OH | (CH₂)₃(1,2-phe)COOH |
| 71 | R | 7-Cl | CH₂CH₂ | S(CH₂)₂CO₂H | S(CH₂)₂(1,1-c-Pen)OH |
| 72 | S | 7-Cl | CH₂CH₂ | SCH₂CH(CH₂CF₃)CO₂H | (CH₂)₂(1,2-phe)CMe₂OH |
| 73 | S | 7-Cl | CH₂CH₂ | S(CH₂)₂CMe₂OH | (CH₂)₂(4-Cl-1,2-phe)CO₂H |
| 74 | R | 7-Cl | CH₂CH₂ | SCH₂(S)CHEtCONHS(O)₂Me | (CH₂)₂(1,2-phe)CMe₂OH |
| 75 | S | 7-Cl | CH₂CH₂ | S(CH₂)₂CMeOH | (CH₂)₂(1,3-phe)CMe₂CO₂H |
| 76 | S | 7-Cl | CH₂CH₂ | S(CH₂)₂CMeOH | (CH₂)₂(1,3-phe)CHMeCO₂H |
| 77 | S | 7-Cl | CH₂CH₂ | S(CH₂)₃CMe₂OH | (CH₂)₂(1,2-phe)CO₂H |
| 78 | S | 7-Cl | CH₂CH₂ | SCH₂(S)CHEtCO₂H | (CH₂)₂(1,4-phe)CMe₂OH |
| 79 | RS | 7-Cl | CH₂CH₂ | S(CH₂)₂CMe₂OH | (CH₂)₂(1,3-phe)CN4H |
| 80 | S | 7-Cl | CH₂CH₂ | S(CH₂)₃CMe₂OH | (CH₂)₂(1,2-phe)CHMeCO₂H |
| 81 | S | 7-Cl | CH₂CH₂ | S(CH₂)₃CMe₂OH | (CH₂)₂(1,2-phe)CHMeCONHS(O)₂CH₃ |
| 82 | S | 7-Cl | CH₂CH₂ | S(CH₂)₂CMe₂OH | (CH₂)₃(1,2-phe)CO₂H |
| 83 | R | 7-Cl | CH₂CH₂ | S(O)₂CH₂(S)CHEtCO₂H | (CH₂)₂(1,2-phe)CMe₂OH |
| 84 | S | 7-Cl | CH₂CH₂ | S(CH₂)₂CMe₂OH | (CH₂)₂(4-Cl-1,2-phe)CHMeCO₂H |
| 85 | S | 7-Cl | CH₂CH₂ | SCH₂(S)CHMeCO₂H | (CH₂)₂(1,2-phe)CH₂CMe₂OH |
| 86 | S | 7-Cl | CH₂CH₂ | S(CH₂)₂CMe₂OH | (CH₂)₂(7,2-phe)CO₂Me |
| 87 | S | 7-Cl | CH₂CH₂ | S(CH₂)₃CMe₂OH | (CH₂)₂(4-Cl-1,2-phe)CO₂H |
| 88 | R | 7-Cl | CH₂CH₂ | S(CH₂)₃CMe₂OH | (CH₂)₂(4-Cl-1,2-phe)CO₂H |
| 89 | S | 7-Cl | CH₂CH₂ | S(CH₂)₃CMe₂OH | (CH₂)₂(1,2-phe)CMe₂CO₂H |
| 90 | S | 7-Cl | CH₂CH₂ | S(CH₂)₂CMe₂OH | (CH₂)₃(R)CHMe₂CO₂H |
| 91 | S | 7-Cl | CH₂CH₂ | S(CH₂)₃CEt₂OH | (CH₂)₂(1,2-phe)CO₂H |
| 92 | S | 7-Cl | CH₂CH₂ | S(CH₂)₃CEt₂OH | (CH₂)₂(1,2-phe)CHMeCO₂H |
| 93 | R | 7-Cl | CH₂CH₂ | SCHMeCH₂CO₂H | (CH₂)₂(1,2-phe)CMe₂OH |
| 94 | S | 7-Cl | CH₂CH₂ | S(CH₂)₃CMe₂OH | (CH₂)₂(1,2-phe)CHEtCO₂H |
| 95 | S | 7-Cl | CH₂CH₂ | S(CH₂)₃CMe₂OH | (CH₂)₂(1,2-phe)CH(n-Pr)CO₂H |
| 96 | S | 7-Cl | CH₂CH₂ | S(CH₂)₃CMe₂OH | (CH₂)₂(1,2-phe)CH(i-Pr)CO₂H |
| 97 | R | 7-Cl | CH₂CH₂ | SCH₂MeCHMeCO₂H | (CH₂)₂(1,2-phe)CMe₂OH |
| 98 | R | 7-Cl | CH₂CH₂ | S(CH₂)₂CMe₂OH | (CH₂)₃(R)CHMeCO₂H |
| 99 | R | 7-Cl | CH₂CH₂ | SCH₂(S)CHMeCN4H | (CH₂)₂(1,2-phe)CMe₂OH |
| 100 | S | 7-Cl | CH₂CH₂ | SCH₂(S)CHMeCO₂H | (CH₂)₂(3-OH-1,4-phe)CHMeOH |
| 101 | S | 7-Cl | CH₂CH₂ | S(CH₂)₃CHMeOH | (CH₂)₂(1,2-phe)CHMeCO₂H |
| 102 | R | 7-Cl | CH₂CH₂ | S(S)CHMeCH₂CO₂H | (CH₂)₂(1,2-phe)CMe₂OH |
| 103 | R | 7-Cl | CH₂CH₂ | S(R)CHMeCH₂CO₂H | (CH₂)₂(1,2-phe)CMe₂OH |
| 104 | R | 7-Cl | CH₂CH₂ | S(S)CHMe(S)CHMeCO₂H | (CH₂)₂(1,2-phe)CMe₂OH |
| 105 | R | 7-Cl | CH₂CH₂ | S(R)CHMe(R)CHMeCO₂H | (CH₂)₂(1,2-phe)CMe₂OH |
| 106 | R | 7-Cl | CH₂CH₂ | SCHEtCH₂CO₂H | (CH₂)₂(1,2-phe)CMe₂OH |
| 107 | S | 7-Cl | CH₂CH₂ | S(CH₂)₃CHMeOH | (CH₂)₂(1,2-phe)CHEtCO₂H |
| 108 | S | 7-Cl | CH₂CH₂ | SCH₂(S)CHMeCO₂H | (CH₂)₂(1,2-phe)CH(OH)CH₂(OH)Ph |
| 109 | R | 7-Cl | CH₂CH₂ | SCMe₂CH₂CO₂H | (CH₂)₂(1,2-phe)CMe₂OH |
| 110 | R | 7-Cl | CH₂CH₂ | SCH₂CHMeCH₂CO₂H | (CH₂)₂(1,2-phe)CMe₂OH |
| 111 | R | 7-Cl | CH₂CMe₂ | SCH₂(1,1-c-Pr)CH₂CO₂H | (CH₂)₂(1,2-phe)CMe₂OH |
| 112 | S | 7-Cl | CMe₂CH₂ | SCH₂(1,1-c-pr)CH₂CO₂H | (CH₂)₂(1,2-phe)CO₂H |
| 113 | S | 7-Cl | CH₂CH₂ | S(CH₂)₃CMe₂OH | (CH₂)₂(1,2-phe)(R)CHEtCO₂H |
| 114 | S | 7-Cl | CH₂CH₂ | S(CH₂)₃CMe₂OH | (CH₂)₂(1,2-phe)(S)CHEtCO₂H |
| 115 | S | 7-Cl | CH₂CH₂ | S(CH₂)₃CMe₂OH | (CH₂)₂(4-Cl-1,2-phe)CHEtCO₂H |
| 116 | S | 7-Cl | CH₂CH₂ | S(CH₂)₃CMe₂OH | (CH₂)₂(1,2-phe)CEt₂CO₂H |

TABLE I-continued

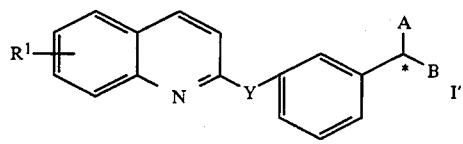

| EX. | * | R¹ | Y | A | B |
|---|---|---|---|---|---|
| 117 | S | 7-Cl | CH₂CH₂ | S(CH₂)₃CMe₂OH | (CH₂)₂(1,2-phe)CH₂CO₂H |
| 118 | S | 7-Cl | CH₂CH₂ | S(CH₂)₃CMe₂OH | (CH₂)₂(1,2-phe)CH(OH)CO₂H |
| 119 | S | 7-Cl | CHMeCHMe | SCH₂(1,1-c-Pr)CH₂CO₂H | (CH₂)₂(1,2-phe)CHEtCO₂H |
| 120 | S | 7-Cl | CH₂CH₂ | S(CH₂)₃CMe₂OH | (CH₂)₂CMeCH₂CO₂H |
| 121 | R | 7-Cl | CH₂CH₂ | SCH₂CMe₂CH₂CO₂H | (CH₂)₂(7,2-phe)CMe₂OH |
| 122 | R | 7-Cl | CH₂CH₂ | S(CH₂)₄CMe₂OH | (CH₂)₂(1,2-phe)CHEtCO₂H |
| 123 | S | 7-F | CH₂CH₂ | SCH₂CMe₂CH₂CO₂H | (CH₂)₂(1,2-phe)CO₂H |
| 124 | S | 7-Br | CH₂CH₂ | SCH₂CMe₂CH₂CO₂H | (CH₂)₂(1,2-phe)CO₂H |
| 125 | S | 7-I | CH₂CH₂ | SCH₂(1,1-c-Pr)CH₂CO₂H | (CH₂)₂(1,2-phe)CMe₂OH |
| 126 | S | 7-CF₃ | CH₂CH₂ | SCH₂CMe₂CH₂CO₂H | (CH₂)₂(1,2-phe)CHMeCO₂H |
| 127 | S | 7-CN | CH₂CH₂ | SCH₂CMe₂CH₂CO₂H | (CH₂)₂(1,2-phe)CHEtCO₂H |
| 128 | S | 7-NO₂ | CH₂CH₂ | SCH₂(1,1-c-Pr)CH₂CO₂H | (CH₂)₂(1,2-phe)CMe₂OH |
| 129 | R | 7-N₃ | CH₂CH₂ | SCH₂(1,1-c-Pr)CH₂CO₂H | (CH₂)₂(1,2-phe)CMe₂OH |
| 130 | RS | 7-Cl | CH₂CH₂ | S(CH₂)₂CMe₂OH | (CH₂)₂CMe₂CH₂CO₂H |
| 131 | R | 7-Cl | CH₂CH₂ | S(1,2-phe)CH₂CO₂H | (CH₂)₂(1,2-phe)CMe₂OH |
| 132 | R | 7-Cl | CH₂CH₂ | S(CH₂)₃CMe₂OH | (CH₂)₂(1,2-phe)CHEtCO₂H |
| 133 | S | 7-Cl | CH₂CH₂ | S(CH₂)₂CMe₂OH | (CH₂)₂(1,2-phe)CHEtCO₂H |
| 134 | S | 7-Cl | CH₂CH₂ | S(CH₂)₃CMe(4-Cl—Ph)OH | (CH₂)₂(1,2-phe)CHEtCO₂H |
| 135 | R | 7-Cl | CH₂CH₂ | SCH₂(1,2-phe)CMe₂OH | (CH₂)₂CMe₂CH₂CO₂H |
| 136 | R | 7-Cl | CH₂CH₂ | SCH₂(1,1-c-Pr)CH₂CO₂H | (CH₂)₂(1,2-phe)CMe₂OH |
| 137 | R | 7-Cl | CH₂CH₂ | SCH₂(1,1-c-Bu)CH₂CO₂H | (CH₂)₂(1,2-phe)CMe₂OH |
| 138 | R | 7-Cl | CH₂CH₂ | SCH₂CMe₂CHMeCO₂H | (CH₂)₂(1,2-phe)CMe₂OH |
| 139 | S | 7-Cl | CH₂CH₂ | SCH₂(1,2-phe)CMe₂OH | (CH₂)₂CMe₂CH₂CO₂H |
| 140 | R | 7-Cl | CH₂CH₂ | SCHMeCMe₂CH₂CO₂H | (CH₂)₂(1,2-phe)CMe₂OH |
| 141 | R | 7-Cl | CH₂CH₂ | S(1,1-c-Pr)CH₂CO₂H | (CH₂)₂(1,2-phe)CMe₂OH |
| 142 | R | 7-Cl | CH₂CH₂ | S(1,1-c-Pr)CHMeCO₂H | (CH₂)₂(1,2-phe)CMe₂OH |
| 143 | R | 7-Cl | CH₂CH₂ | S(1,1-c-Pr)CH₂CO₂H | (CH₂)₂(1,3-phe)CMe₂OH |
| 144 | R | 7-Cl | CH₂CH₂ | S(1,1-c-Pr)CH₂CO₂H | (CH₂)₂(1,2-phe)(1,1-c-Bu)OH |
| 145 | R | 7-Cl | CH₂CH₂ | S(1,1-c-Pr)CH₂CO₂H | (CH₂)₂(1,3-phe)(1,1-c-Bu)OH |
| 146 | R | 7-Cl | CH₂CH₂ | SCH₂(1,1-c-Pr)CH₂CO₂H | (CH₂)₂(1,3-phe)CMe₂OH |
| 147 | R | 7-Cl | CHCH₂CH | SCH₂(1,1-c-Pr)CH₂CO₂H | (CH₂)₂(1,2-phe)CMe₂OH |
| 148 | R | 7-Cl | CHCH₂CH | S(1,1-c-Pr)CH₂CO₂H | (CH₂)₂(1,2-phe)CMe₂OH |
| 149 | R | 7-Cl | CHCH₂CH | SCMe₂CH₂CO₂H | (CH₂)₂(1,2-phe)CMe₂OH |
| 150 | R | 7-Cl | CHCH₂CH | S(1,1-c-Pr)(S)CHMeCO₂H | (CH₂)₂(1,2-phe)CMe₂OH |
| 151 | R | 7-Cl | CHCH₂CH | S(1,1-c-Pr)CHMeCO₂H | (CH₂)₂(1,3-phe)CMe₂OH |
| 152 | R | 7-Cl | CHCH₂CH | S(1,1-c-Pr)CH₂CO₂H | (CH₂)₂(1,2-phe)(1,1-c-Bu)OH |
| 153 | R | 7-Cl | CHCH₂CH | S(1,1-c-Pr)CH₂CO₂H | (CH₂)₂(1,3-phe)(1,1-c-Bu)OH |
| 154 | S | 7-Cl | CH₂CH₂ | SCH₂CHEtCO₂H | (CH₂)₂(1,2-phe)CMe₂OH |
| 155 | S | 7-Cl | CH₂CH₂ | SCH₂(1,2-phe)CMe₂OH | CH₂)₂(1,2-phe)CHEtCO₂H |
| 156 | S | 7-Cl | CH₂CH₂ | S(CH₂)₂CMe₂OH | (CH₂)₂(1,2-phe)CH₂CO₂H |
| 157 | S | 7-Cl | CH₂CH₂ | SCH₂(1,2-phe)CHMe₂OH | (CH₂)₂(1,2-phe)CH₂CO₂H |
| 158 | S | 7-Cl | CH₂CH₂ | S(CH₂)₂CMe₂OH | (CH₂)₂(4-Cl-1,2-phe)CH₂CO₂H |
| 159 | S | 7-Cl | CH₂CH₂ | SCH₂(1,2-phe)CMe₂OH | (CH₂)₂(4-Cl-1,2-phe)CH₂CO₂H |
| 160 | R | 7-Cl | CH₂CH₂ | SCH₂CMe₂CH₂CO₂H | (CH₂)₄(1,2-phe)CMe₂OH |
| 161 | S | 7-Cl | CH₂CH₂ | S(CH₂)₃CMe₂OH | (CH₂)₂(4-Cl-1,2-phe)CH₂CO₂H |
| 162 | S | 7-Cl | CH₂CH₂ | SCH₂(1,2-phe)CMe₂OH | (CH₂)₂(1,1-c-Pr)CH₂CO₂H |

TABLE II
ELEMENTAL ANALYSES

| EX. | FORMULA | CALCULATED | | | FOUND | | |
|---|---|---|---|---|---|---|---|
| | | C | H | N | C | H | N |
| 66 | C₃₂H₃₃ClNO₃SNa.3.5H₂O | 60.70 | 6.37 | 2.21 | 60.38 | 6.43 | 2.44 |
| 70 | C₃₃H₃₅ClNO₃SNa.0.5H₂O | 66.82 | 6.12 | 2.36 | 66.72 | 6.14 | 2.19 |
| 73 | C₃₃H₃₂Cl₂NO₃SNa.H₂O | 61.73 | 5.50 | 2.25 | 61.97 | 5.70 | 2.20 |
| 102 | C₃₃H₃₅ClNO₃SNa.H₂O | 65.82 | 6.19 | 2.33 | 66.10 | 6.32 | 2.16 |
| 109 | C₃₄H₃₇ClNO₃SNa.2.0H₂O | 64.39 | 6.52 | 2.21 | 64.31 | 6.53 | 2.30 |
| 121 | C₂₅H₃₄ClNO₃SNa.1.5H₂O | 65.77 | 6.42 | 2.19 | 65.47 | 6.14 | 2.17 |
| 136 | C₃₅H₃₇ClNO₃SNa.H₂O | 66.98 | 6.22 | 2.23 | 67.31 | 6.05 | 2.43 |
| 139 | C₃₅H₃₉ClNO₃SNa.1.0H₂O | 66.70 | 6.56 | 2.22 | 66.83 | 6.50 | 2.28 |
| 142 | C₃₅H₃₇ClNO₃SNa.1.5H₂O | 66.03 | 6.28 | 2.20 | 66.19 | 6.46 | 2.60 |
| 147 | C₃₆H₃₇ClNO₃SNa.2.5H₂O | 65.00 | 6.06 | 2.10 | 65.43 | 6.40 | 2.23 |
| 148 | C₃₅H₃₅ClNO₃SNa.1.5H₂O | 66.18 | 6.03 | 2.21 | 66.04 | 6.13 | 2.13 |
| 150 | C₃₄H₃₃ClNO₃SNa.H₂O | 66.71 | 5.76 | 2.29 | 66.17 | 5.87 | 2.16 |
| 154 | C₃₄H₃₇ClNO₃SNa.3.5H₂O | 61.76 | 6.70 | 2.12 | 61.52 | 6.54 | 1.93 |
| 158 | C₃₃H₃₄Cl₂NO₃SNa.2.5H₂O | 59.73 | 5.92 | 2.11 | 59.77 | 5.87 | 2.24 |
| 159 | C₃₈H₃₆Cl₂NO₃SNa.H₂O | 65.33 | 5.48 | 2.00 | 65.21 | 5.69 | 2.03 |
| 160 | C₃₇H₄₃ClNO₃SNa.0.4H₂O | 68.64 | 6.82 | 2.16 | 68.62 | 6.86 | 2.16 |
| 161 | C₃₄H₃₆Cl₂NO₃SNa.2.0H₂O | 61.07 | 6.03 | 2.09 | 61.17 | 6.09 | 1.92 |

TABLE II-continued

| | | ELEMENTAL ANALYSES | | | | |
|---|---|---|---|---|---|---|
| | | CALCULATED | | | FOUND | |
| EX. | FORMULA | C | H | N | C | H | N |
| 162 | $C_{35}H_{37}ClNO_3SNa.2.0H_2O$ | 65.05 | 6.40 | 2.17 | 65.45 | 6.20 | 2.10 |

Methods of Synthesis

Compounds of the present invention can be prepared according to the following methods. Temperatures are in degree Celsius.

Method A

Bromo acid II is treated with 2 equivalents of a base such as n-butyllithium in a suitable solvent such as THF at −100° C., then at −78° C. to afford III, which is reacted with IV (see EP 206,751, Dec. 30, 1986; EP 318,093, May 31, 1989, and U.S. Pat. No. 4,851,409, Jul. 25, 1989) to yield the hydroxyacid V. V is then esterified using conditions such as methanol/HCl, $CH_2N_2$ or $MeI/K_2CO_3$ and an organometallic reagent is then added to give the diol VI. The benzylic alcohol of VI is then reacted with the thiol IX by: (1) making the chloride by reaction with methanesulfonyl chloride in the presence of triethylamine, and (2) substituting the chloride by the thiol IX in the presence of a base such as sodium hydride or cesium carbonate to afford VII. In the cases where $Q^1$ is an ester, hydrolysis with a base such as NaOH, LiOH or $K_2CO_3$ (followed by acidification) affords the acid VIII. VII and VIII are both representatives of structure I.

Method B

The ketone IV is reduced to the benzylic alcohol using a reagent such as $NaBH_4$. This benzylic alcohol is converted to the benzylic bromide, using conditions such as carbon tetrabromide/1,2-bis-(diphenylphosphino)ethane, and treatment with triphenylphosphine affords the phosphonium salt X. Using a base such as potassium hexamethyldisilazide, the ylid of X is formed and is added to a lactol. Oxidation of the benzylic alcohol so obtained using conditions such as (1) $MnO_2$ in EtOAc and (2) $MnO_2/HCN/MeOH$ affords the ester XI. The thiol IX is then added to XI using a Lewis acid such as $AlCl_3$ or $TiCl_4$ to give the thioether XII. Reaction of XII with an organometallic compound such as a lithium or a magnesium salt, yield, in the cases where $Q^1$ is stable in these conditions, the tertiary alcohol XIII, which is a representative of structure I.

Method C

The ester XXVII, obtained by Method E, is hydrolyzed with a base such as NaOH to give XIV. XIV is reacted with another organometallic and the reaction mixture is quenched with chlorotrimethyl-silane to yield the hydroxyketone XV. The benzylic alcohol is then reacted with methanesulfonyl chloride in the presence of a base such as triethylamine. The mesylate so obtained is substituted by the thiolate derivative of IX to afford XVI. Finally, an organometallic reaction or a reduction using a reagent such as $NaBH_4$ on XVI gives the alcohol XVIII. Using this method, two different R groups can be added to give a secondary or an unsymmetrical tertiary alcohol.

Method D

The hydroxyacid XVII (included within the definition of XIV) is cyclized to the lactone XXI using a reagent such as 2-chloro-N-methylpyridinium iodide. An organometallic reagent is then added to XXI to give the diol XXII. Finally, the secondary alcohol is substituted by the thiol IX as in Method C to yield the thioether XX.

Method E

The aldehyde XXIII, a derivative of IV, is reacted with an organometallic reagent and the benzylic alcohol so obtained is oxidized to XXIV with an oxidant like activated manganese dioxide. XXIV is then reacted with the iodide XXV in the presence of a base such as lithium diisopropylamide to yield the alkylation product XXVI. Reduction with sodium borohydride or addition of an organometallic reagent afford the hydroxyester XXVII, which is then treated as the lactone XXI in Method D to give the thioether XXVIII.

Method F

The enolate of the ketone XXIX, obtained by treatment of XXIX with a base such as KH or NaH, is reacted with dimethylcarbonate to yield the ketoester XXX. XXX is enolized with a base such as NaH and treated with the iodide XXXI, the methyl ester of XXV. The adduct so obtained is then decarboxylated using conditions such as heating with HCl in acetic acid to afford a mixture of the ester XXXII and the corresponding acid. Esterification of the mixture, using a reagent such as diazomethane or methyl iodide and $K_2CO_3$, yields XXXII, which is then converted to XXXIII or its epimer, as described in Method G.

Method G

The hydroxy acid XVII is esterified using conditions such as heating with MeI and $K_2CO_3$ or reacting with diazomethane. Treatment of this hydroxyester with an oxidant such as activated manganese dioxide affords the ketoester XXXIV. The ketone is then reduced using the chiral oxazaboro-lidine XXXV in the presence of borane/THF complex. Reaction of the ester with an organometallic gives the diol XXXVI, which is chiral XXII. Protection of the secondary alcohol with tert-butyl-chlorodiphenyl-silane in the presence of a base such as 4-(dimethyl-amino)pyridine, protection of the tertiary alcohol as the 2-tetrahydropyranyl ether and removal of the silyl ether afford XXXVII. The chiral center of XXXVII can be inverted to give XXXVIII using conditions such as: (1) treatment with triphenyl-phosphine, diethyl azodicarboxylate and an acid such as R—(—)α-methoxyphenylacetic acid (chiral acid improves the resolution), and (2) hydrolysis of the ester so obtained with a base such as NaOH. Formation of the mesylate and substitution with the thiol IX as in Method C, followed by hydrolysis of the 2-tetrahydropyranyl ether using conditions such as pyridinium p-toluenesulfonate in methanol afford the thioethers XXXIXa and XXXIXb.

Method H

The phenylacetic acid XL is reduced to the alcohol XLI using a reagent such as borane in tetrahydrofuran. Formation of the alcoholate with one equivalent of a Grignard reagent, followed by treatment with magnesium afford the dimagnesium salt of XLI. It is added to a ketone or an aldehyde to yield the alcohol XLII. The bromide XLIII is then formed using conditions such as (1) formation of the mesylate with methanesulfonyl chloride and triethylamine and (2) substitution of the mesylate by sodium bromide in N,N-dimethyl formamide. The dimagnesium salt of XLIII is then formed as previously described and added to the ketone IV. The adduct XLIV is then-reacted with the thiol IX as in Method C to yield XLV.

Method I

The ketoester XXX is treated with the iodide XLVI and decarboxylated as in Method F. Reduction of the ketone with a reagent such as $NaBH_4$ yields the alcohol XLVII. By reaction with an organometallic in toluene, the nitrile XLVII is converted to the amine XLVIII. The thiol IX is then added as in Method C to afford XLIX. Reaction of an iodide with the amine XLIX gives a secondary or tertiary amine L. Both XLIX and L are representative of structure I.

Method J

Vinylmagnesium bromide or allylmagnesium bromide is added to the aidehyde derivative of IV to yield LI. Using the procedure of R.C. Larock et al. (Tetrahedron Letters, 30, 6629 (1989)), the aryl halide LII is coupled to the alcohol LI to give LIII. When $Q^3$ is an ester or an alcohol, LIII can be converted to LIV or its isomer, a structure representative of Ia, using the procedure of Method G. Also, when $Q^3$ is $Q^1$, chiral reduction of the ketone LIII with XXXV as in Method G followed by formation of the mesylate and substitution by the thiol LV afford LVI, a structure representative of Ib.

In the following schemata

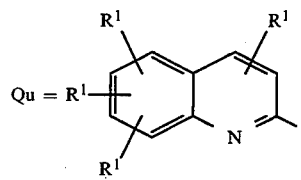

METHOD A

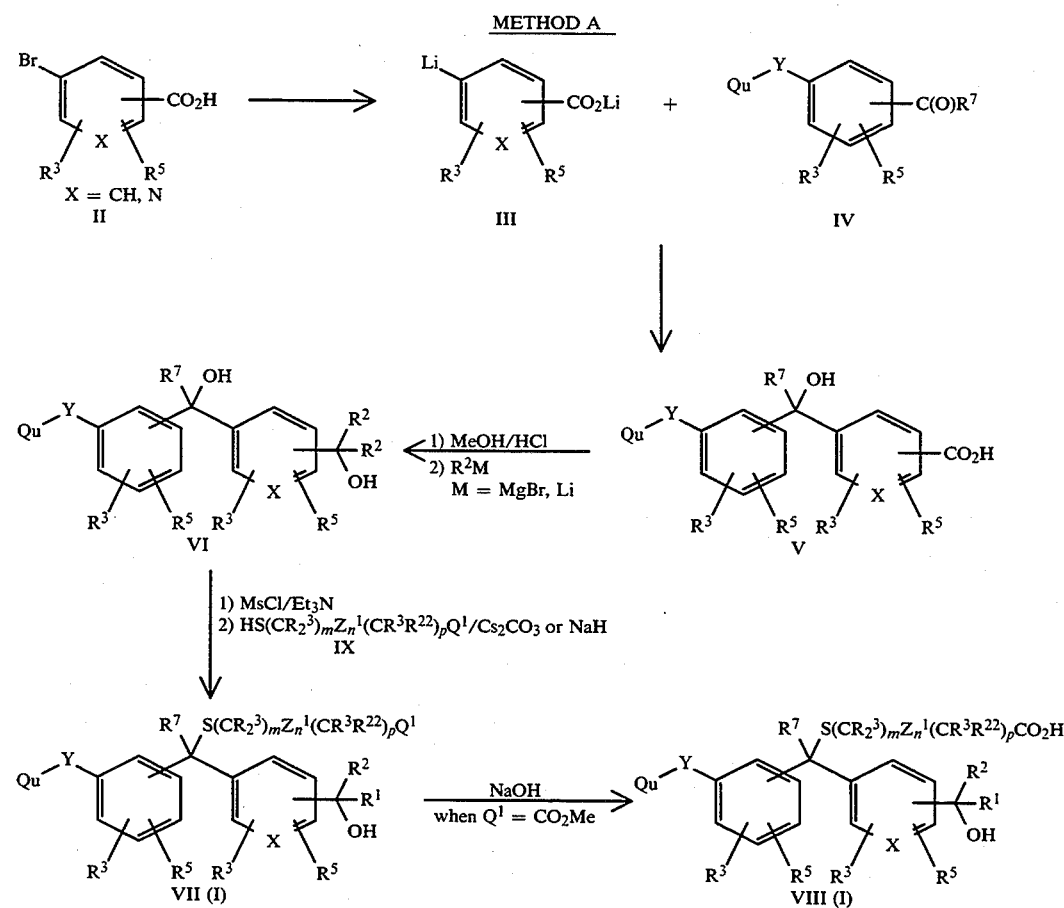

Method B
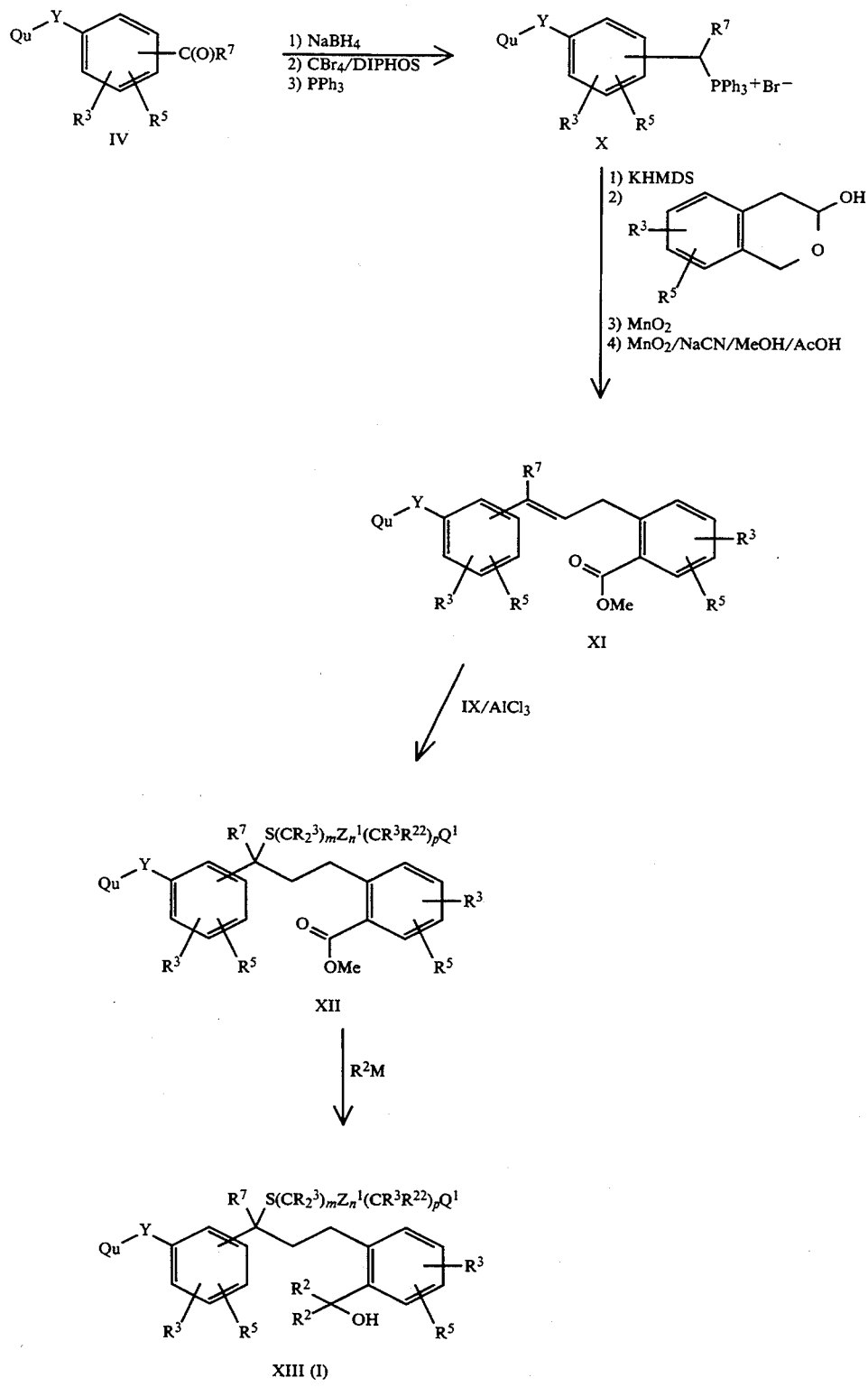

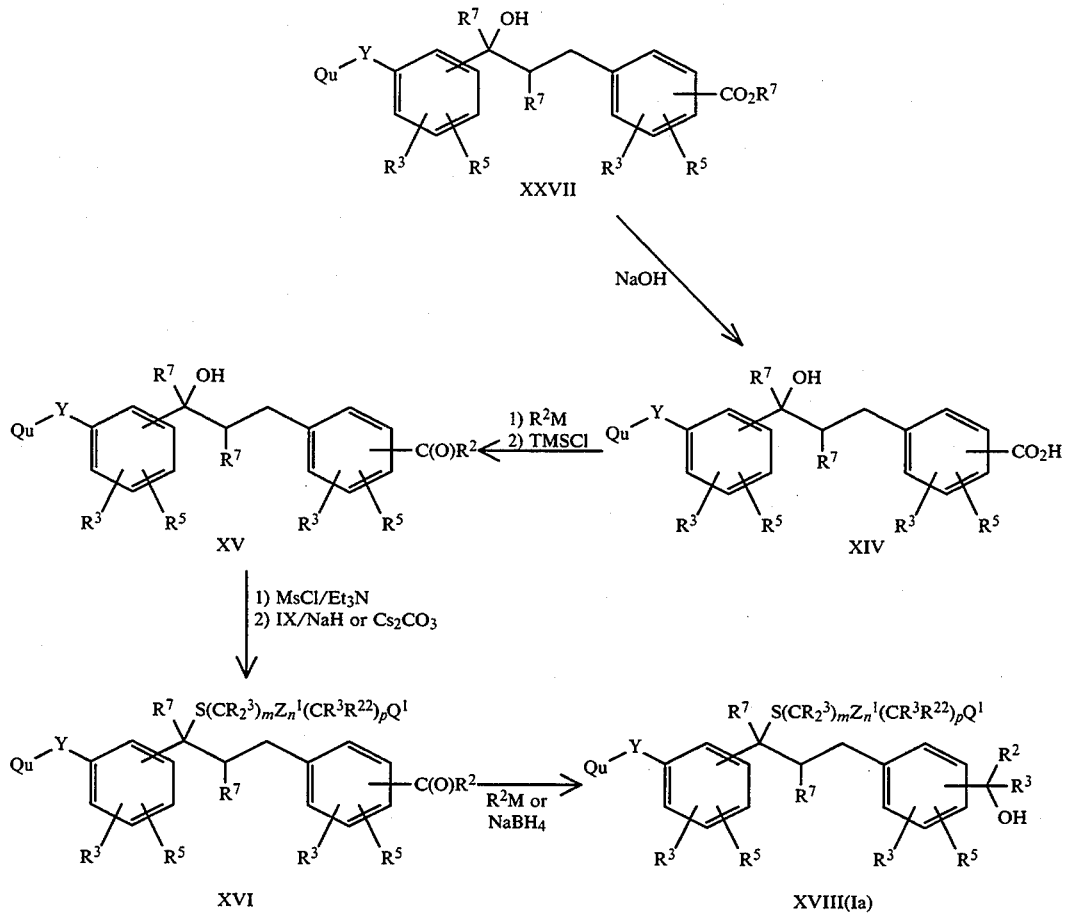
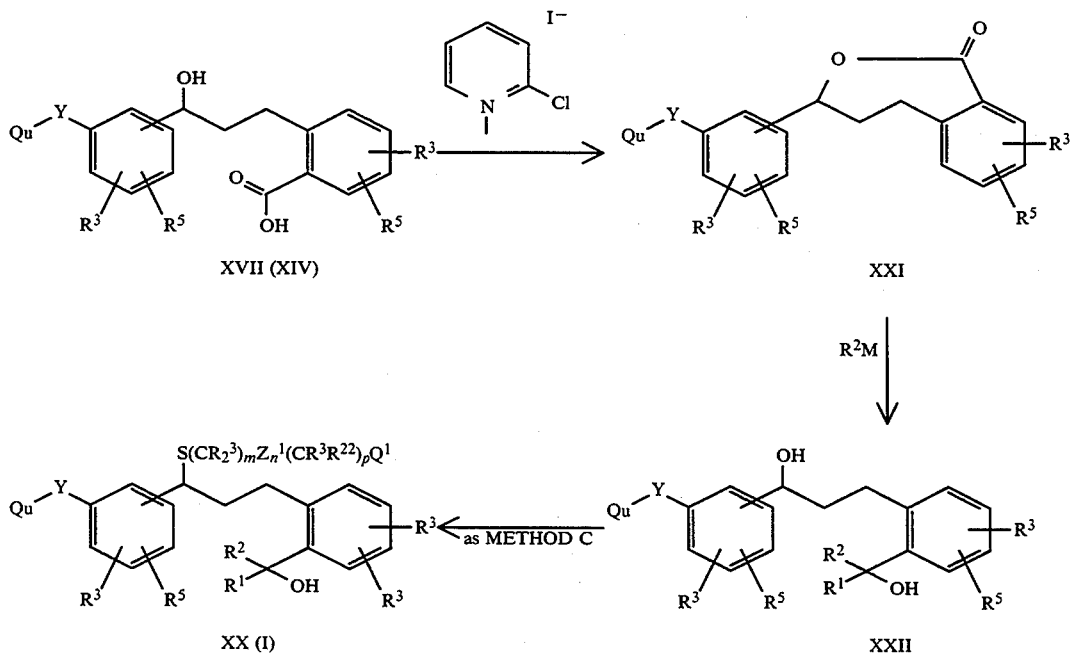

METHOD E
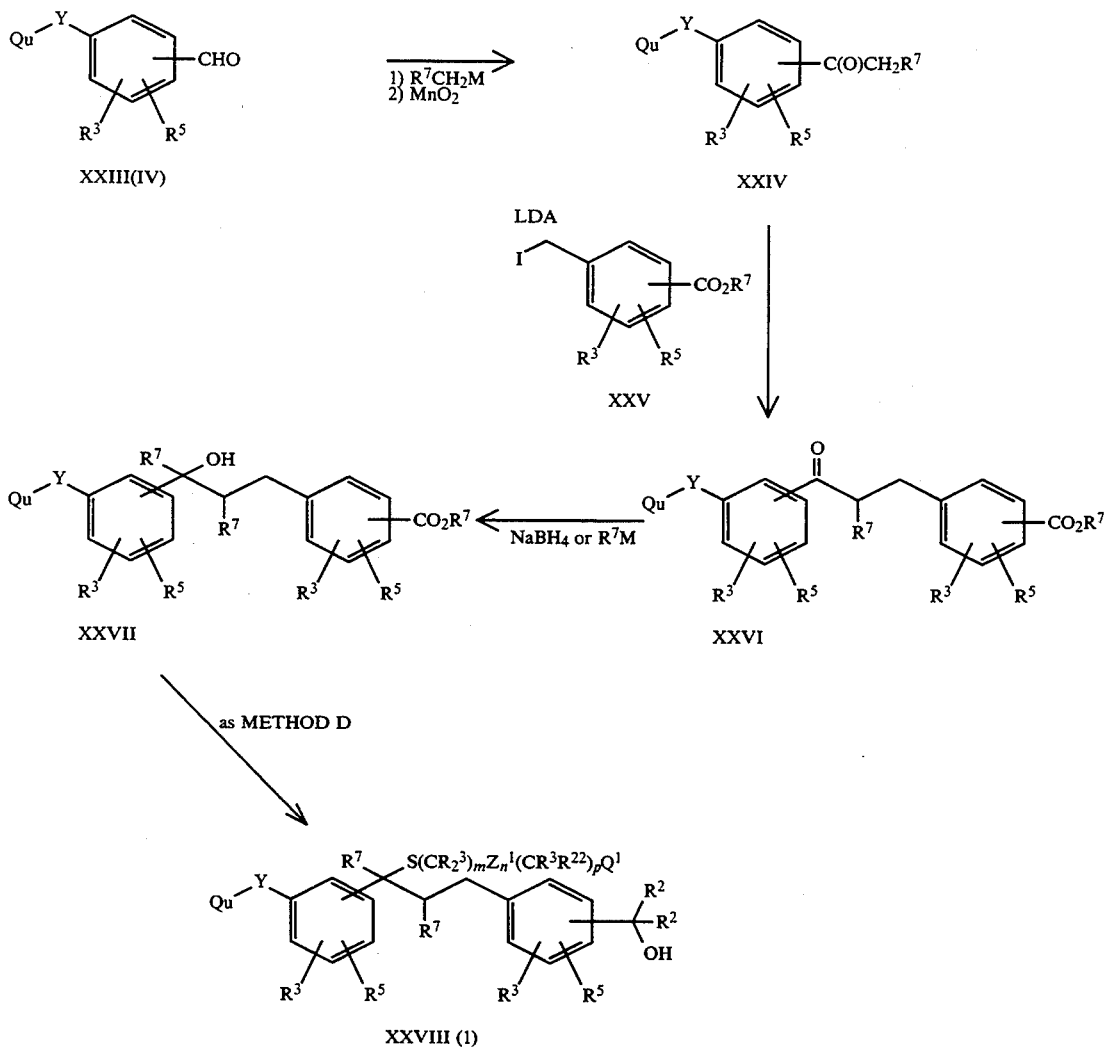
METHOD F
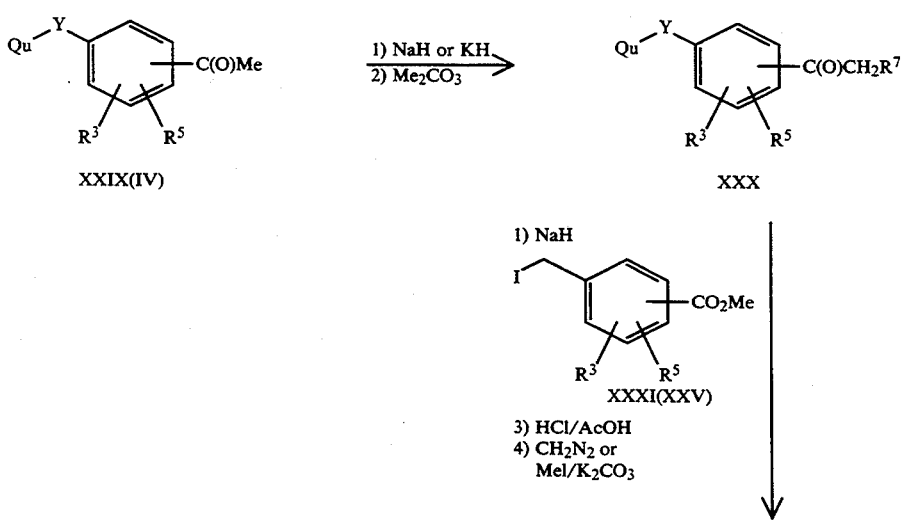

-continued
METHOD F
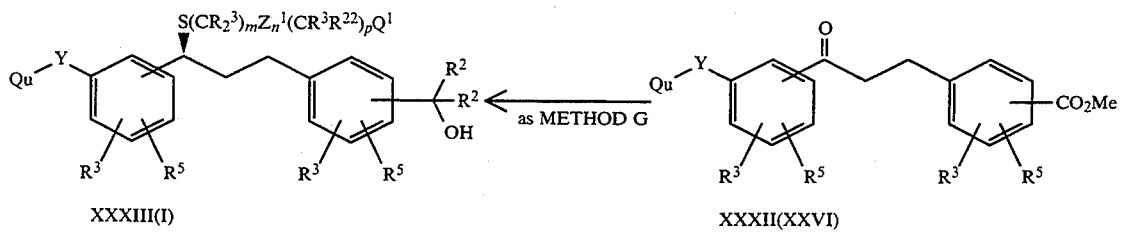
METHOD G
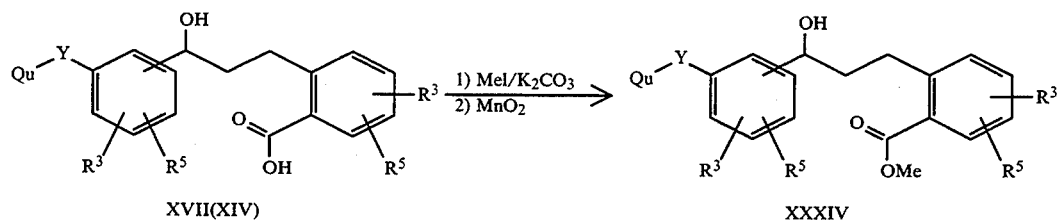
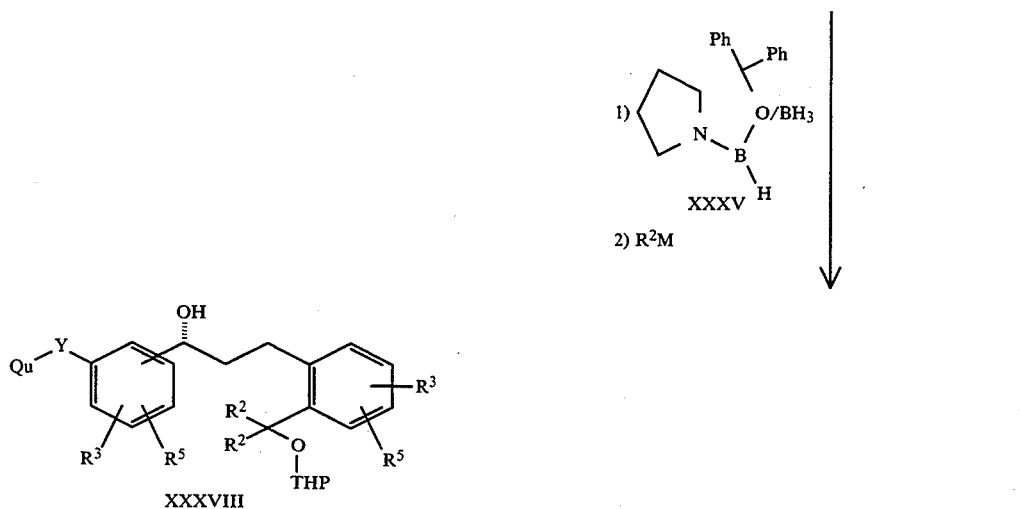
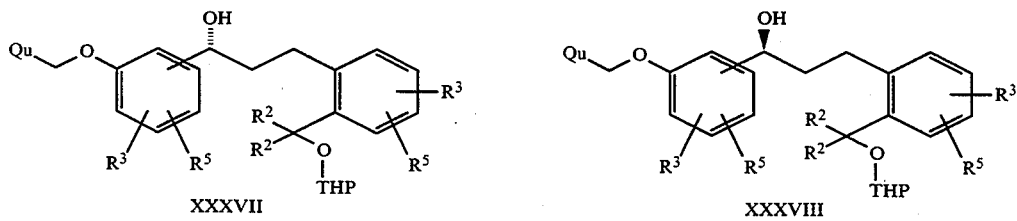
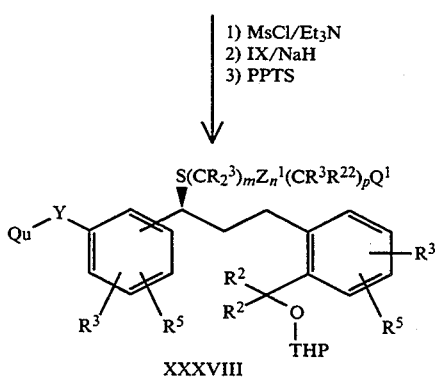

METHOD G
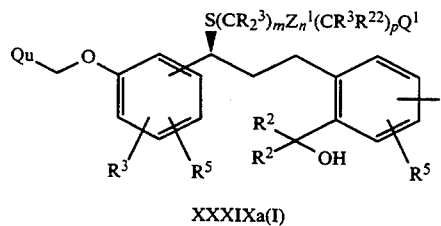
XXXIXa(I)
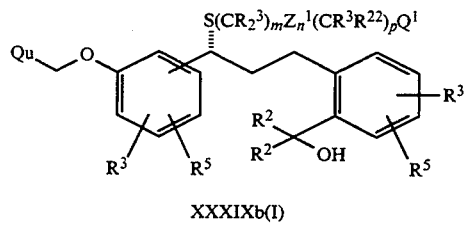
XXXIXb(I)
METHOD H
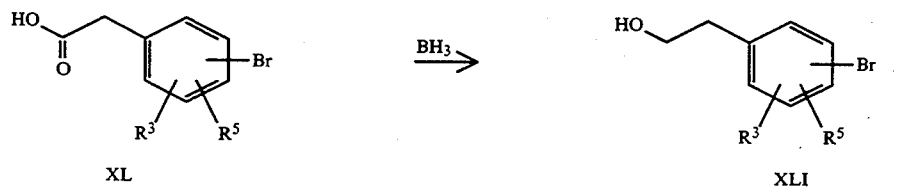
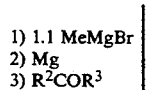
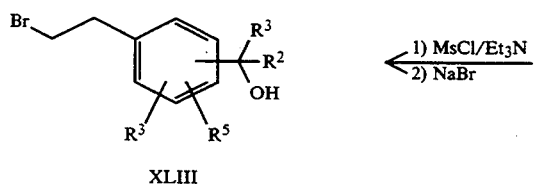
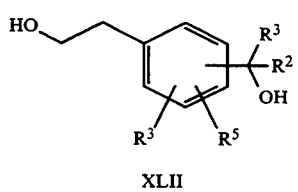
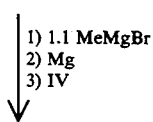
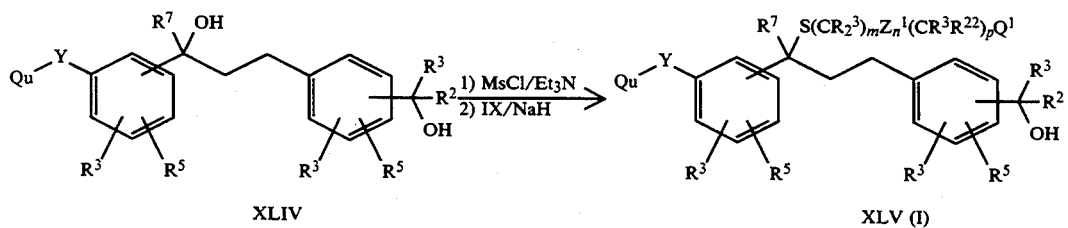

METHOD I
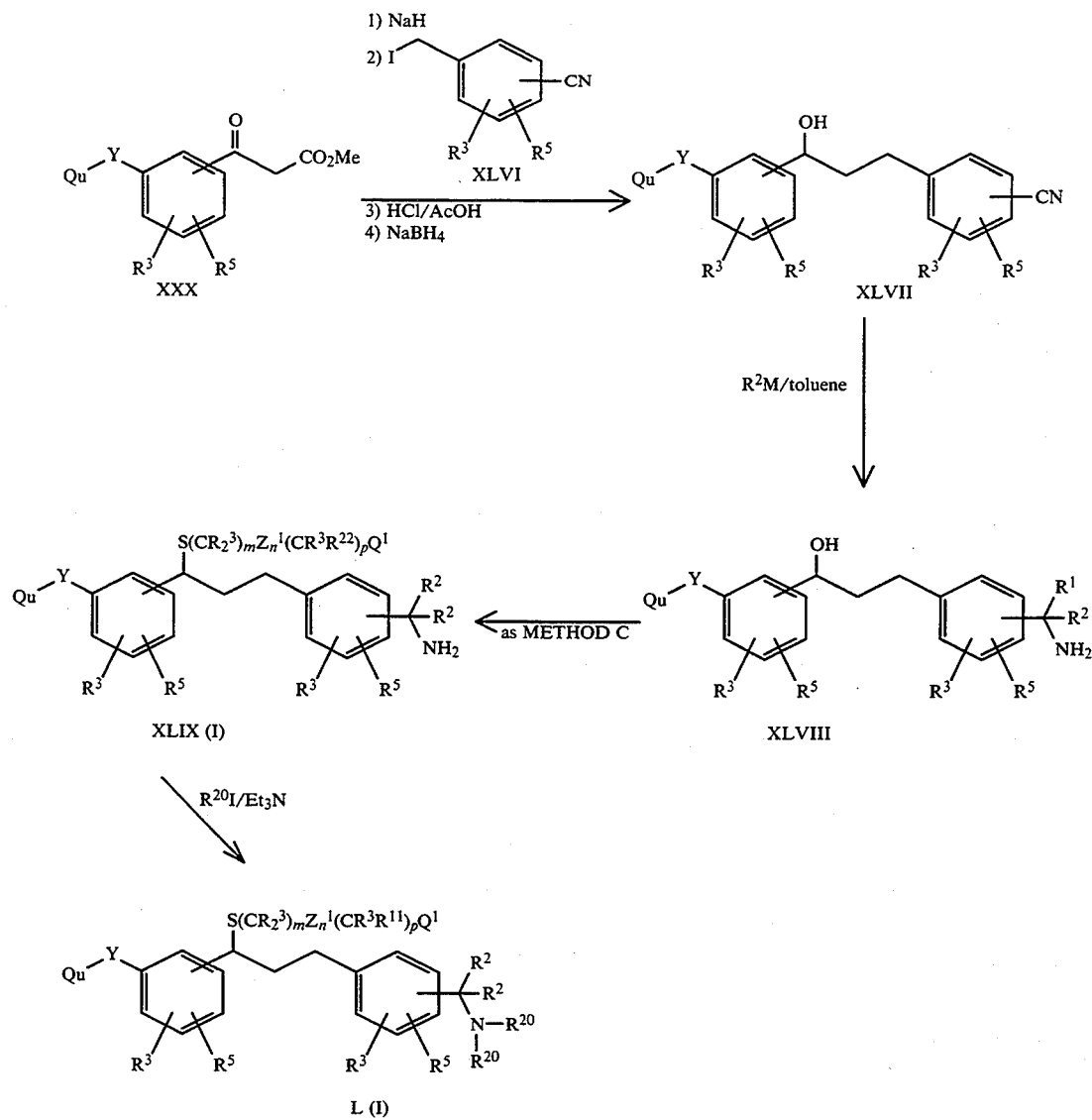
METHOD J
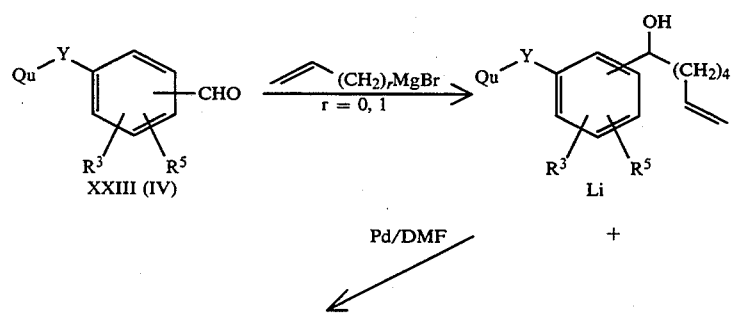

-continued
METHOD J

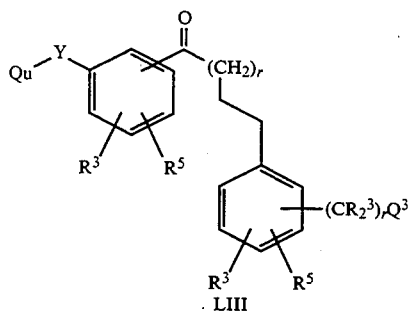

LIII

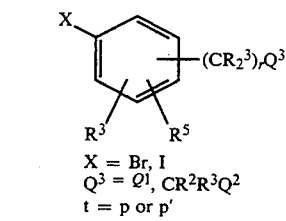

X = Br, I
$Q^3 = Q^1, CR^2R^3Q^2$
t = p or p'

LII $Q^3 = CO_2Me, CR^2R^3OH$
as in METHOD G $Q^3 = Q^1$
1) chiral reduction
2) MsCl/Et$_3$N
3) $HS(CR_2^3)_m\text{-}Z_n^2(CR^3R^4)_pCR^2R^3OH$
    (LV)/NaH or $Cs_2CO_3$

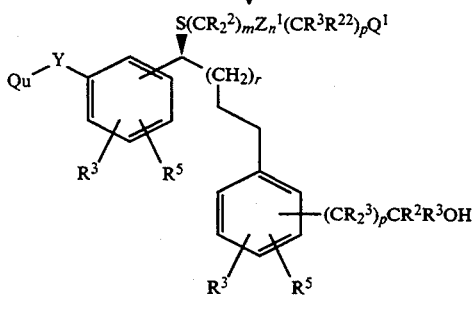

LIV (Ia)

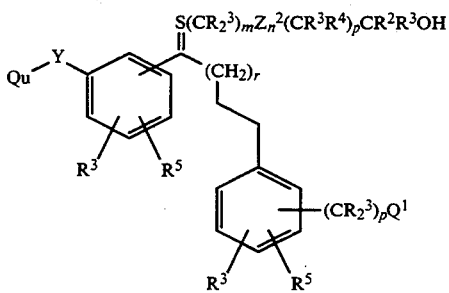

LVI (Ib)

Assays for Determining Biological Activity

Compounds of Formula I can be tested using the following assays to determine their mammalian leukotriene antagonist activity and their ability to inhibit leukotriene biosynthesis.

The leukotriene antagonist properties of compounds of the present invention were evaluated using the following assays.

LTD$_4$ Receptor Binding Studies in Guinea Pig Lung Membranes, Guinea Pig Trachea and In vivo Studies in Anesthetized Guines Pigs.

A complete description of these three tests is given by T.R. Jones et al., Can. J. Physiol. Pharmacol., 67, 17–28 (1989).

Compounds of Formula I were tested using the following assays to determine their mammalian leukotriene biosynthesis inhibiting activity.

Determination of Inhibition of 5-Lipoxygenase

The activity of 5-lipoxygenase was measured from the conversion of [$^{14}$C]-arachidonic acid to 5-HETE and 5,12-diHETEs catalyzed by the 10,000×g supernatant fraction from rat PMN leukocytes, using the procedure of Riendeau and Leblanc (Biochem. Biophys. Res. Comun., 141, 534–540, (1986)) with minor modifications. The incubation mixture contained 25 mM Na$^+$/K$^+$phosphate buffer, pH 7.3, 1 mM ATP, 0.5 mM CaCl$_2$, 0.5 mM mercaptoethanol and an aliquot of the enzyme preparation in a final volume of 0.2 ml. The enzyme was pre-incubated with the inhibitor for 2 min at 37° C. before initiation of the reaction with the addition of 2 ml of [$^{14}$C]-arachidonic acid (25,000 DPM) in ethanol to obtain a final concentration of 10 mM. Inhibitors were added as 500-fold concentrated solutions in DMSO. After incubation for 10 min at 37° C., the reaction was stopped by adding 0.8 mL of diethyl ether/methanol/1 M citric acid (30:4:1). The samples were centrifuged at 1,000×g for 5 min and the organic phases analyzed by TLC on Baker Si250F-PA or Whatman silica gel 60A LKGF plates using diethyl ether/petroleum ether/acetic acid (50:50:1) as solvent. The amount of radioactivity migrating at the positions of arachidonic acid, 5-HETE and 5,12-diHETEs was determined using a Berthold TLC analyzer LB 2842. The activity of 5-lipoxygenase was calculated from the percentage of conversion of arachidonic acid to 5-HETE and 5,12-diHETEs after the 10 min incubation.

Human Polymorphonuclear (PMN) Leukocyte LTB$_4$ Assay

A. Preparation of Human PMN

Human blood was obtained by antecubital venepuncture from consenting volunteers who had not taken medication within the previous 7 days. The blood was immediately added to 10% (v/v) trisodium citrate (0.13 M) or 5% (v/v) sodium heparin (1000 IU/mL). PMNs were isolated from anticoagulated blood by dextran sedimentation of erythrocytes followed by centrifugation through Ficoll-Hypaque (specific gravity 1.077), as described by Boyum.[1] Contaminating erythrocytes were removed by lysis following exposure to ammonium chloride (0.16 M) in Tris buffer (pH 7.65), and the PMNs resuspended at 5 ×10$^5$ cells/mL in HEPES (15 mM)-buffered Hanks balanced salt solution containing Ca$^{2+}$(1.4 mM) and Mg$^{2+}$(0.7 mM), pH 7.4. Viability was assessed by Trypan blue exclusion and was typically greater than 98%.

B. Generation and Radioimmunoassay of LTB$_4$

PMNs (0.5 mL; 2.5×10$^5$ cells) were placed in plastic tubes and incubated (37° C., 2 min) with test compounds at the desired concentration or vehicle (DMSO, final concentration 0.2%) as control. The synthesis of LTB$_4$ was initiated by the addition of calcium ionophore A23187 (final concentration 10 mM) or vehicle in control samples and allowed to proceed for 5 minutes at 37° C. The reactions were then terminated by the addition of cold methanol (0.25 mL) and samples of the entire PMN reaction mixture were removed for radioimmunoassay of LTB$_4$.

Samples (50 mL) of authentic LTB$_4$ of known concentration in radioimmunoassay buffer (RIA) buffer (potassium phosphate 1 mM; disodium EDTA 0.1 mM; Thimerosal 0.025 mM; gelatin 0.1%, pH 7.3) or PMN reaction mixture diluted 1:1 with RIA buffer were added to reaction tubes. Thereafter [$^3$H]-LTB$_4$ (10 nCi in 100 mL RIA buffer) and LTB4-antiserum (100 mL of a 1:3000 dilution in RIA buffer) were added and the tubes vortexed. Reactants were allowed to equilibrate by incubation overnight at 4° C. To separate antibody-bound from free LTB$_4$, aliquots (50 mL) of activated charcoal (3% activated charcoal in RIA buffer containing 0.25% Dextran T-70) were added, the tubes vortexed, and allowed to stand at room temperature for 10 minutes prior to centrifugation (1500×g; 10 min; 4° C.). The supernatants containing antibody-bound LTB$_4$ were decanted into vials and Aquasol 2 (4 mL) was added. Radioactivity was quantified by liquid scintillation spectrometry. Preliminary studies established that the amount of methanol carried into the radioimmunoassay did not influence the results. The specificity of the antiserum and the sensitivity of the procedure have been described by Rokach et al.[2] The amount of LTB$_4$ produced in test and control (approx. 20 ng/10$^6$ cells) samples were calculated. Inhibitory dose-response curves were constructed using a four-parameter algorithm and from these the IC$_{50}$ values were determined.

Compounds of Formula I were tested in the following assays to determine their in vivo activity as both leukotriene antagonist and leukotriene biosynthesis inhibitor.

(1) Boyum, A. *Scand. J. Clin. Lab. Invest.*, (21 (*Supp* 97), 77 (1968).

(2) Rokach, J.; Hayes, E.C.; Girard, Y.; Lombardo, D.L.; Maycock, A.L.; Rosenthal, A.S.; Young, R.N.; Zamboni, R.; Zweerink, H.J. *Prostalglandins Leukotrienes and Medicine*, 13, 21 (1984).

Asthmatic Rat Assay

Rats are obtained from an inbred line of asthmatic rats. Both female (190-250 g) and male (260-400 g) rats are used.

Egg albumin (EA), grade V, crystallized and lyophilized, is obtained from Sigma Chemical Co., St. Louis. Aluminum hydroxide is obtained from the Regis Chemical Company, Chicago. Methysergide bimaleate was supplied by Sandoz Ltd., Basel.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilhiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 mL of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 mL of a suspension containing 1 mg EA and 200 mg aluminum hydroxide in saline. They are used between days 12 and 24 postsensitization. In order to eliminate the serotonin component of the response, rats are pretreated intravenously 5 minutes prior to aerosol challenge with 3.0 mgm/kg of methysergide. Rats are then exposed to an aerosol of 3% EA in saline for exactly 1 minute, then their respiratory profiles are recorded for a further 30 minutes. The duration of continuous dyspnea is measured from the respiratory recordings.

Compounds are generally administered either orally 1-4 hours prior to challenge or intravenously 2 minutes prior to challenge. They are either dissolved in saline or 1% methocel or suspended in 1% methocel. The volume injected is 1 mL/kg (intravenously) or 10 mL/kg (orally). Prior to oral treatment rats are starved overnight. Their activity is determined in terms of their ability to decrease the duration of symptoms of dyspnea in comparison with a group of vehicle-treated controls. Usually, a compound is evaluated at a series of doses and an ED$_{50}$ is determined. This is defined as the dose (mg/kg) which would inhibit the duration of symptoms by 50%.

Pulmonary Mechanics in Trained Conscious Squirrel Monkeys

The test procedure involves placing trained squirrel monkeys in chairs in aerosol exposure chambers. For control purposes, pulmonary mechanics measurements of respiratory parameters are recorded for a period of about 30 minutes to establish each monkey's normal control values for that day. For oral administration, compounds are dissolved or suspended in a 1% methocel solution (methylcellulose, 65HG,400 cps) and given in a volume of 1 ml/kg body weight. For aerosol administraiton of compounds, a DeVilbiss ultrasonic nebulizer is utilized. Pretreatment periods vary from 5 minutes to 4 hours before the monkeys are challenged with aerosol doses of either leukotriene D$_4$ (LTD$_4$) or Ascaris antigen.

Following challenge, each minute of data is calculated by computer as a percent change from control values for each respiratory parameter including airway resistance (R$_L$) and dynamic compliance (C$_{dyn}$). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of LTD$_4$ or Ascaris antigen response by the test compound. For statistical analysis, paired t-test is used. (References: McFarlane, C.S. et al., *Prostaglandins*, 28, 173-182

(1984) and McFarlane, C.S. et al., Agents Actions, 22, 63–68 (1987)).

Prevention of Induced Bronchoconstriction in Allergic Sheep

A. Rationle:

Certain allergic sheep with known sensitivity to a specific antigen (*Ascaris suum*) respond to inhalation challenge with acute and late bronchial responses. The time course of both the acute and the late bronchial responses approximates the time course observed in asthmatics and the pharmacological modification of both responses is similar to that found in man. The effects of antigen in these sheep are largely observed in the large airways and are conveniently monitored as changes in lung resistance or specific lung resistance.

B. Methods:

Animal Preparation: Adult sheep with a mean weight of 35 kg (range, 18 to 50 kg) are used. All animals used meet two criteria: a) they have a natural cutaneous reaction to 1:1,000 or 1:10,000 dilutions of *Ascaris suum* extract (Greet Diagnostics, Lenois, NC) and b) they have previously responded to inhalation challenge with *Ascaris suum* with both an acute bronchoconstriction and a late bronchial obstruction (Abraham, W.M., Delehunt, J.C., Yerger, L. and Marchette, B., Am. Rev. Resp. Dis., 128, 839–44 (1983)).

Measurement of Airway Mechanics: The unsedated sheep are restrained in a cart in the prone position with their heads immobilized. After topical anesthesia of the nasal passages with 2% lidocaine solution, a balloon catheter is advanced through one nostril into the lower esophagus. The animals are then intubated with a cuffed endotracheal tube through the other nostril using a flexible fiberoptic bronchoscope as a guide. Pleural pressure is estimated with the esophageal balloon catheter (filled with one ml of air), which is positioned such that inspiration produces a negative pressure deflection with clearly discernible cardiogenic oscillations. Lateral pressure in the trachea is measured with a sidehole catheter (inner dimensions, 2.5 man) advanced through and positioned distal to the tip of the nasotracheal tube. Transpulmonary pressure, the difference between tracheal pressure and pleural pressure, is measured with a differential pressure transducer (DP45; Validyne Corp., Northridge, Calif.). Testing of the pressure transducer catheter system reveals no phase shift between pressure and flow to a frequency of 9 Hz. For the measurement of pulmonary resistance ($R_L$), the maximal end of the nasotracheal tube is connected to a pneumotachograph (Fleisch, Dyna Sciences, Blue Bell, Pa). The signals of flow and transpulmonary pressure are recorded on an oscilloscope (Model DR-12; Electronics for Medicine, White Plains, N.Y.) which is linked to a PDP-11 Digital computer (Digital Equipment Corp., Maynard, Mass.) for on-line calculation of $R_L$ from transpulmonary pressure, respiratory volume obtained by integration and flow. Analysis of 10–15 breaths is used for the determination of $R_L$. Thoracic gas volume ($V_{tg}$) is measured in a body plethysmograph, to obtain specific pulmonary resistance ($SR_L = R_L \cdot V_{tg}$).

Aerosol Delivery Systems: Aerosols of *Ascarie suum* extract (1:20) are generated using a disposable medical nebulizer (Raindrop ®, Puritan Bennett), which produces an aerosol with a mass median aerodynamic diameter of 6.2 μM (geometric standard deviation, 2.1) as determined by an electric size analyzer (Model 3030; Thermal Systems, St. Paul, Minn.). The output from the nebulizer is directed into a plastic t-piece, one end of which is attached to the nasotracheal tube, the other end of which is connected to the inspiratory part of a Harvard respirator. The aerosol is delivered at a tidal volume of 500 ml of a rate of 20 per minute. Thus, each sheep receives an equivalent dose of antigen in both placebo and drug trials.

Experimental Protocol: Prior to antigen challenge baseline measurements of $SR_L$ are obtained, infusion of the test compound is started 1 hr prior to challenge, the measurement of $SR_L$ repeated and then the sheep undergoes inhalation challenge with *Ascaris suum* antigen. Measurements of $SR_L$ are obtained immediately after antigen challenge and at 1,2,3,4,5,6,6.5,7,7.5 and 8 hr after antigen challenge. Placebo and drug tests are separated by at least 14 days. In a further study, sheep are given a bolus dose of the test compound followed by an infusion of the test compound for 0.5–1 hr prior to ascaris challenge and for 8 hr after ascaris as described above.

Statistical Analysis: A Kruskal-Wallis one way ANOVA test was used to compare the acute immediate responses to antigen and the peak late response in the controls and the drug treated animals.

The invention is further defined by reference to the following examples, which are intended to be illustrative and not limiting. All temperatures are in degrees Celsius.

EXAMPLE 13

Sodium 3-((1-(3-(2-(7-chloro-2-quinolinyl)ethyl)-phenyl)-3- (2-(2-hydroxy-2- propyl)phenyl)propyl)thio)-2-methylpropanoate Step 1: Ethyl 3-(acetylthio)-2-methylpropanoate Ethyl 2-methylpropenoate (39 mmol) was diluted with 5.6 mL (78 mmol) of thiolacetic acid and stirred at 65° C. for 36 h. The mixture was then diluted with ether, washed with water and the organic phase was dried with Na$_2$SO$_4$. Evaporation to dryness yielded the title material as an orange oil which was used as such for the next step.

Step 2: Ethyl 3-mercapto-2-methylpropanoate

At −20° C., 3N NaOH (150 mL, 450 mmol) was added dropwise to a solution of ethyl 3-(acetyl-thio)-2-methylpropanoate (66.47 g, 349 mmol, Step 1) in 700 mL of MeOH and the mixture was stirred at that temperature for 30 min. 25% Aq NH$_4$OAc was then added and the title thiol was extracted with EtOAc, dried over MgSO$_4$, concentrated and distilled to yield 42.52 g (82%) of the title compound as an oil; bp: 96–98° C./15 mmHg. $^1$H NMR (CDC13): δ1.21–1.36 (6H, m), 1.50 (1H, t, SH), 2.66 (2H, m), 2.81 (1H, m), 4.19 (2H, q).

Step 3: 3- Mercapto-2- methylpropanoic acid

A mixture of the ester of Step 2 (6.67 mmol) and 1.0N NaOH (13 mL) in 55 mL of MeOH:THF 3:2 was stirred at r.t. for 24 h. 25% Aq NH$_4$OAc was then added and the mixture was acidified with HOAc. The title acid was extracted with EtOAc and dried over Na$_2$SO$_4$. Kugelrohr distillation at 100° C./15 mm Hg yielded the title compound as a colorless oil. $^1$H NMR (CDC13): δ1.30 (3H, d), 1.58 (1H, t), 2.8 (3H, m), 10.3 (1H, very br s).

Step 4: 3-((1-(3-(2-(7-chloro-2-quinolinyl)ethyl)-phenyl)3; - (2-(methoxycarbonyl) phenyl)propyl)-thio)2-methylpropanoic acid At −10° C., AlCl$_3$ (2.437 g, 18.3 mmol) was added to a solution of methyl 2-(3-(3-(2-(7-chloro-2-quinolinyl)ethyl)phenyl)-2-propenyl)benzoate (EP 318,093, May 31, 1989, Example 36, Step 1) (1.013 g, 2.28 mmol) and 3-mercapto-2-methylpropanoic acid (356 mg, 2.96 mmol (Step 3) in 25 mL of CH$_2$Cl$_2$ and the mixture was stirred at 0° C. in the dark for 2 h. Cold aq NH$_4$OAc, EtOAc an THF were then added and the mixture was stirred until complete dissolution of the oil. The product was extracted with EtOAc:THF 1:1, dried over Na$_2$SO$_4$ and concentrated. The sodium salt of the acid was formed in EtOH with 500 μL of 10N NaOH. It was purified on an Amberlite ion exchange resin XAD-8. Elution with water separated the sodium 3-mercapto-2-methylpropanoate and elution with methanol afforded the title acid as an impure sodium salt. The compound was dissolved in saturated aq NH$_4$Cl, extracted with EtOAc:THF 1:1, dried over Na$_2$SO$_4$ and purified by flash chromatography on silica using acetone:toluene:HOAc 5:95:1 to yield 766 mg (60%) of the title acid.

Step 5: 3-((1-(3-(2-(7-chloro-2-quinolinyl)ethyl)-phenyl)3-(2-(2-(hydroxy-2- propyl)phenyl)-propl)-thio)-2-methylpropanoic acid To the ester of Step 4 (626 mg, 1.11 mmol) dissolved in 10 mL of THF at 0° C., 1.5 M MeMgBr (4.0 mL, 6.0 mmol) was added slowly and the mixture was stirred at 0° C. for 2 h and at r.t. for 2 h. At 0° C., aq saturated NH$_4$Cl was added and the product was extracted with EtOAc, dried over Na$_2$SO$_4$ and purified by flash chromatography on silica using acetone:toluene:HOAc 5:95:1 and 7.5:92.5:1. The pure title compound was finally obtained by HPLC on a μ-Porasil column (diameter: 12 mm; flow rate: 8.9 ml min$^{-1}$) using acetone:toluene:HOAc 5:95:1. Yield: 246 mE, 39%.

Step 6:

To the acid of Step 5 (243 mg, 431 mmol) in 10 mL of EtOH was added 1.0 N NaOH (430 μl ). The solvents were evaporated and the product was freeze-dried to give 250 mg of the title compound as a yellowish solid. Anal. calcd for C$_{33}$H$_{35}$NO$_3$ScClNa•1.5H$_2$O: C, 64.85; H, 6.27; N, 2.29. Found: C, 64.29; H, 6.26; N, 2.21.

EXAMPLE 14

Sodium 3-((1-(3-(2-(7-chloro-2-quinolinyl)ethyl)phenyl-phenyl)-3-(2-(2-hydroxy-2-propyl)phenyl)propyl)-thio)-propanoate Step 1: Methyl 3-((1-(3-(2-(7-chloro-2-quinolinyl)-ethyl) phenyl)-3-(2-(methoxycarbonyl)phenyl)-propyl)thio)proanoate Using the procedure of Example 13, Step 4, but avoiding the purification on ion exchange resin, methyl 3-mercaptopropanoate was added to methyl 2-(3-(3-(2-(7-chloro-2-quinolinyl)ethyl)phenyl)-2-propenyl)benzoate (Example 13, Step 4) to give the title compound in 77% yield. $^1$H NMR (CD$_3$COCD$_3$): δ2.08 (2H, m), 2.45 (411, m), 2.75 (1H, m), 2.90 (1H, m), 3.20 (2H, m), 3.30 (211, m), 3.60 (3H, s), 3.82 (3H, s), 3.88 (1H, dd), 7.15–7.33 (6H, m), 7.38–7.50 (3H, m), 7.84 (1H, d), 7.87 (1H, d), 7.98 (1H, br s), 8.20 (1H, d).

Step 2: 3-((1-(3-(2-(7-chloro-2-quinolinyl)ethyl)-phenyl)-3-(2-(methoxycarboxyl) phenyl)propyl)-thio)propanoic acid The diester of Step 1 (875 mg, 1.56 mmol) was dissolved in 75 mL of MeOH and 7.5 mL of THF. At room temperature, aqueous 1M K$_2$CO$_3$ (15 mL, 15 mmol) was added and the mixture was stirred overnight. The mixture was concentrated under reduced pressure and then neutralized with HCl1M and saturated aqueous NH$_4$Cl until pH=5–6. The acid ester was extracted with EtOAc (3×20 mL) and the organic phase was dried over MgSO$_4$, filtered and evaporated to give an oil. Purification by flash chromatography on silica gel with EtOAc:Toluene:Acetone:HCOOH (10:83:7:0.2) yielded 605 mg (71% yield) of the title compound. $^1$H NMR (CD$_3$COCD$_3$): δ2.08 (2H, m), 2.46 (4H, m), 2.75 (1H, m), 2.90 (1H, m), 3.18 (2H, m), 3.30 (2H, m), 3.80 (3H, s), 3.90 (1H, dd), 7.15–7.32 (6H, m), 7.38–7.50 (3H, m), 7.82 (1H, d), 7.87 (1H, d), 8.0 (1H, br s), 8.19 (1H, d).

Step 3

The acid ester of Step 2 was converted to the tertiary alcohol as in Example 13, Step 5. This alcohol was purified as the t-butyldiphenylsilyl ester. The formation of the silyl ester was effected with t-butyldiphenylsilyl chloride, triethylamine and 4-dimethylaminopyridine in CH$_2$Cl$_2$. Hydrolysis was done with tetrabutylammonium fluoride in HOAc and THF. Finally, the title compound was obtained as in Example 13, Step 6. Anal. calcd for C$_{32}$H$_{33}$NO$_3$SClNa•0.5H$_2$O: C, 66.37; H, 5.92; N, 2.42. Found: C, 66.15; H, 5.62; N, 2.24.

EXAMPLE 73

2-(3-(S)-(3-(2-(7-chloro-2-quinolinyl)ethyl)phenyl)-3-((3-hydroxy-3-methylbutyl)thio) propyl )-5-chloro-benzoic acid The title compound was prepared according to Example 158, but using methyl 2-bromo-5-chlorobenzoate.

EXAMPLE 102

3-(S)-( (l(R)-(3-(2-(7-chloro-2-quinolinyl)ethyl)-phenyl-3-(2-(2-hydroxy-2-propyl) phenyl)propyl)thio)-butanoic acid Step 1: Methyl 3(S)-(acetylthio)butanoate To a −23° C. solution of PPh$_3$ (40 mmol, 10.48 g) in THF (100 mL) was added DEAD (diethylazodicarboxylate) (40 mmol, 6.28 mL) dropwise and the mixture was stirred at −23° C. for 16 h, during which time a white precipitate was obtained. A THF (30 mL) solution of methyl 3(R)-hydroxybutyrate (20 mmol, 2.36 g) and thiolacetic acid (40 mmol, 2.85 mL) was slowly added and the mixture was allowed to slowly warm to 25° C. and was stirred 16 h at 25° C. Most of the THF was removed in vacuo and EtOAc (10 mL) and hexanes (100 mL) were added. Insolubles were removed by filtration and the residue was purified by chromatography on silica gel to afford the title compound (yield: 45%). [α]$_D^{25}$ = −21 ° (c=3, CHCl$_3$). $^1$H NMR (acetone d$_6$) δ1.30 (3H, d), 2.25 (3H, s), 2.45–2.80 (2H, m), 3.62 (3H, s), 3.75–3.95 (1H, m).

Step 2:

The title compound was prepared according to Method J, starting from 3-(2-(7-chloro-2-quino-linyl)ethyl)benzaldehyde (Example 158) and methyl 3(S)-mercaptobutanoate, obtained by reaction of methyl 3(S)-(acetylthio)butanoate with hydrazine in MeCN to deprotect the thiol.

EXAMPLE 10

3-((1 (R)-(3-(2-(7-chloro-2-quino-linyl)ethyl)phenyl)-3-(2-(2-hydroxy-2-propyl) phenyl)propyl)thio)-3-methylbutanoic acid Step, 1: 3-Benzylthio-3-methylbutanoic acid A solution of 3,3-dimethylacrylic acid (7 g, 70 mmol) and benzyl mercaptan (8.9 mL, 7.5 mmol) in piperidine (70 mL) was heated to reflux for 2 days. The piperidine was then evaporated and the product was partitioned between EtOAc and an aqueous solution of 1N HCl. The organic phase was washed with brine and dried over MgSO$_4$. After evaporation of the solvent the product was distilled with a Kugelrohr apparatus under high vacuum (1 mmHg) to give 15.5 g of the title compound (99% yield). $^1$H NMR (CDCl$_3$) δ1.50 (6H, s), 2.67 (2H, s), 3.82 (2H, s), 7.30 (SH, m).

Step 2: 3-Mercapto-3l-methylbutanoic acid

Approximately 300 mL of NH$_3$ was condensed in a three-neck flask maintained at −70° C. Then, 8.3 g of Na (0.35 mol) was added in small pieces and with very vigorous stirring. The 3-benzylthio-3-methylbutanoic acid from Step 1 (15.5 g, 69 mmol) dissolved in THF (50 mL) was added dropwise at −78° C. The deep blue solution was stirred for 1 h at −78° C. and solid NH$_4$Cl and an aqueous solution of NH$_4$Cl was added until the blue color vanished. The solution was then warmed to room temperature and the ammonia was evaporated with a stream of nitrogen. The reaction mixture was then acidified with HOAc, extracted with EtOAc, washed with brine and dried over MgSO$_4$. The solvent was evaporated and the residual oil was used without further purification. $^1$H NMR (CDCl3) δ1.50 (6H, s), 2.38 (1H, s) and 2.72 (2H, s).

Step 3:

The title compound was prepared according to Example 102, but using 3-mercapto-3-methyl butanoic acid.

EXAMPLE 121

4-((1 (R)-(3-(2-(7-chloro-2-quinolinyl )ethyl)phenyl)-3-(2-(2-hydroxy-2-propyl) phenyl)propyl)thio)-3,3-dimethylbutanoic acid Step 1: Methyl 3,3-dimethyl-4-hydroxybutanoiate To a suspension of LAH (lithium aluminum hydride) (4.9 g, 0.129 mol) in THF (300 mL) maintained at −78° C. was slowly added (45 min) a solution of 2,2-dimethylsuccinic anhydride (16.5 g, 0.129 mol) in THF (350 mL). After 45 min of vigorous stirring the reaction mixture was warmed to −60° C. and poured into 1 M aqueous sodium potassium tartrate (500 mL) and stirred for 2 h at r.t. The mixture was then acidified with HOAc (150 mL) and extracted three times with EtOAc. The combined organic phases were washed with brine and dried over Na$_2$SO$_4$. The residual oil was dissolved in Et$_2$O and a solution of diazomethane in Et$_2$O (about 300 mL, 0.15 mol) was added until the yellow color remained. An aqueous solution of NH$_4$Cl was added and the ester was extracted with EtOAc and dried over MgSO$_4$. The oil was purified by flash chromatography with 2:3 EtOAc:hexane to yield the title compound (13.5 g, 72%). $^1$H NMR (CDCl3) δ1.00 (6H, s), 2.33 (3H, br s), 3.42 (2H, s), 3.70 (3H, s).

Step 2: Methyl 4-( acetylthio)-3,3-dimethylbutanoate

To a solution of PPh$_3$ (107.8 g, 0.411 mol) in THF (700 mL) maintained at 0° C. was added dropwise DEAD (64.7 mL, 0.411 mol) and the mixture was stirred at 0° C. for 30 min until the complex was precipitated. A solution of the alcohol of Step 1 (30 g, 0.205 mol) and thiolacetic acid (29.4 mL, 0.411 mol) in THF (300 mL) was then added dropwise (mechanical stirring). After 4 days at 4° C. the reaction mixture was evaporated to dryness, the white precipitate was suspended in 30:1 hexane:EtOAc and filtered. The residual oil was then purified by a flash chromatography using toluene then 100:1 toluene:EtOAc to yield the title compound. Yield: 31 g, 74%. $^1$H NMR (CDCl$_3$) δ1.05 (6H, s), 2.27 (2H, s), 2.37 (3H, s), 3.00 (2H, s), 3.65 (3H, s).

Step 3:

The title compound was prepared according to Example 102, but using methyl 3,3-dimethyl-4-mercapto- butanoate obtained by hydrazine treatment of methyl 3,3-d imethyl-4-( acetylthio) butanoate.

EXAMPLE 136

1-(((1(R)-(3-(2-(7-chloro-2-quinol inyl)ethyl)phenyl)-3-(2-(2-hydroxy-2-propyl) phenyl)propyl)thio)methyl) -cycylopropaneacetic acid Step 1: 1,1-cyclopropanedimethanol A solution of LiAlH$_4$ (50 g, 1.32 mol) in 1.6 L of THF was cooled to −18° C. under N$_2$. A solution of diethyl 1,1-cyclopropanedicarboxylate (175 g, 0.94 mol) in 1.2 L of THF was then added dropwise over 50 min, at such a rate that the internal temperature of the reaction remained below 10° C. The cooling bath was then removed, and after 15 min, the temperature reached 15° C. The reaction was then quenched by careful addition of 50 mL H$_2$O, followed by 50 mL of 15% NaOH, and then 150 mL of H$_2$O. After the mixture turned white, it was filtered through celite and the bed was washed with 4 L of THF. Evaporation gave an oil which was distilled to give 81 g (0.79 mol, 84%) of the title compound as a colorless oil, b.p. 131–138° C./15 mmHg. $^1$H NMR (CDCl$_3$) δ0.48 (4H, s), 3.30 (2H, s), 3.58 (4H, s).

Step 2: 1-(hydroxymethyl)cyclopropanemethyl benzoate

To a solution of the diol of Step 1 (81 g, 0.79 mol) and pyridine (96 mL, 1.19 mol) in CH$_2$Cl$_2$ (1 L) cooled at 0° C. was added slowly benzoyl chloride (121 mL, 1.03 mol). The reaction mixture was warmed to r.t. overnight and then poured into an aqueous solution of NH$_4$Cl. The products were extracted in CH$_2$Cl$_2$, washed with brine and dried over Na$_2$SO$_4$. The residual oil was purified by flash chromatography with 2:1 hexane:EtOAc and then 1:2 hexane:EtOAc to yield first, 116 g (47% yield) of the diester, then 89 g (54% yield) of the title alcohol. $^1$H NMR (CDCl$_3$) δ0.65 (4H, m), 2.20 (1H, t), 3.53 (2H, d), 4.35 (2H, s), 7.45 (2H, m), 7.60 (1H, m), 8.07 (2H, m).

Step 3: 1-(benzoyloxymethyl)cyclopropaneacetonitrile

To a solution of the alcohol of Step 2 (80 g, 0.388 mol) and Et$_3$N (162 mL, 1.16 mol) in CH$_2$Cl$_2$ (1.5 L) cooled at −40° C. was added methanesulfonyl chloride (75 mL, 0.504 mol). The reaction mixture was warmed to −10° C. for 20 min and then poured into an aqueous solution of NaHCO$_3$ and extracted with CH$_2$Cl$_2$. The organic phases were washed with brine and dried over Na$_2$SO$_4$. The residual oil was then dissolved in DMSO (1.5 L) and NaCN was added (86 g, 1.76 mol) portionwise. The reaction mixture was stirred at r.t. for 3 days then poured in an aqueous solution of NaHCO$_3$ and extracted with Et$_2$O. The organic phases were washed with brine and dried over Na$_2$SO$_4$. Evaporation of the solvent afforded the title product. $^1$H NMI (CDCl$_3$) δ0.80 (4H, m), 2.62 (2H, s), 4.27 (2H, s), 7.48 (2H, m), 7.60 (1H, m), 8.08 (2H, m).

Step 4: Methyl 1-(hydroxymethyl)cyclopropaneacetate

The nitrile of Step 3 (0.388 mol) was dissolved in ethanol (400 mL), 8N KOH (800 mL) was added and the reaction mixture was heated to reflux overnight. Most of the ethanol was evaporated and ice was added to the mixture. Concentrated HCl was added (600 mL) dropwise at 0° C. (without warming over 10° C. inside the solution) until obtention of pH approx. 1. The acid was then extracted with EtOAc two times and the organic phases were washed 2 times with brine and dried over Na$_2$SO$_4$. The solvent was evaporated and the solid was dissolved in THF (500 mL). A solution of diazomethane in Et₂O (about 1.7 L, 0.85 mol) was added at 0° C. until the yellow color remained and no more acid could be seen by TLC. The solvent was evaporated and the residual oil was purified by flash chromatography using 1:1 to 2:1 EtOAc:hexane to yield 28.2 g, (50% yield) of the title compound. $^1$H NMR (CDCl₃) δ0.55 (4H, m), 2.45 (2H, s), 2.55 (1H, t), 3.5 (2H, d), 3.70 (3H, s).

Step 5: Methyl 1-(acetylthiomethyl)cyclopropaneacetate

To a solution of the alcohol of Step 4 (28.2 g, 0.20 mol) and Et₃N (82 mL, 0.59 mol) in CH₂Cl₂ (1 L) cooled to −40° C. was added methanesulfonyl chloride (43.5 mL, 0.3 mol). The reaction mixture was warmed to −10° C. for 20 min and then an aqueous solution of NaHCO₃ was added. The product was extracted with CH₂Cl₂, washed with brine and dried over Na₂SO₄. A portion of this mesylate (0.053 mol) was then dissolved in DMF (180 mL) and cooled to 0° C. Freshly prepared cesium thiol acetate (J. Org. Chem., 51, 3664, (1986)) (22 g, 0.11 mol) was added and the mixture was stirred overnight at r.t. The reaction mixture was poured into an aqueous solution of NaHCO₃ and extracted with Et₂O. The organic phases were washed with brine and dried over Na₂SO₄. The residual oil was then purified by flash chromatography with 10:1 hexane:EtOAc to yield 7.5 g, 70%, of the title compound. $^1$H NMR (CDCl₃) δ0.60 (4H, m), 2.30 (2H, s), 2.35 (3H, s), 3.03 (2H, s), 3.70 (3H, s).

Step 6:

The title compound was prepared according to Example 102, but using methyl 1-(mercaptomethyl)cyclopropaneacetate, generated by hydrazine treatment of methyl 1-(acetylthiomethyl)cyclopropaneacetate.

EXAMPLE 141

1-((1(R)-(3-(2-(7-chloro-2-quinolinyl)ethyl)phenyl)-3-(2-(2-hydroxy-2-propyl) phenyl)propyl)thio)cyclpropaneacetic acid Step 1: Methyl 1-(acetylthio)cyclopropaneacetate A solution of 8.7 g of methyl cyclopropylidene acetate (Tetrahedron Lett. 1986, 27, 1281) in 11.1 mL of thioacetic acid was heated at 85° C. for 2 h and then distilled with a Vigreux column to give an orange oil, b.p. 90° C./250 mmHg. The title compound was obtained by flash chromatography of this orange oil with 5:1 hexane:EtOAc, to give a colorless oil. $^1$H NMR (CDCl₃) δ1.00 (4H, two m), 2.28 (3H, s), 2.65 (2lt, s) and 3.70 (3H, s).

Step 2:

The title compound was prepared according to Example 102, but using methyl 1-mercaptocyclopropaneacetate, generated from methyl 1-(acetylthio)cyclo-propaneacetate.

EXAMPLE 158

2-(3-(S)-(3-(2-(7-chloro-2-quinolinyl)ethyl)phenyl)-3-((3-hydroxy-3-methylbutyl) thio) propyl)-5-chlorophenylacetic acid The title compound was prepared according to Method J, with 3-(2-(7-chloro-2-quinolinyl)ethyl)-benzaldehyde, methyl 2-bromo-5-chlorophenyl acetate, and 3-hydroxy-3-methyl butanethiol as starting materials. 3-(2-(7-chloro-2-quinolinyl)ethyl)-benzaldehyde was prepared by, first, deprotonation of 7-chloro-2-quinaldine with lithium diisopropylamide and alkylation with 3-cyanobenzyl bromide, followed by reduction of the nitrile with DIBAL in toluene.

3-hydroxy-3-methylbutanethiol was prepared by reacting MeMgBr on methyl 3-mercapto propanoate.

What is claimed is:

1. A compound of the formula:

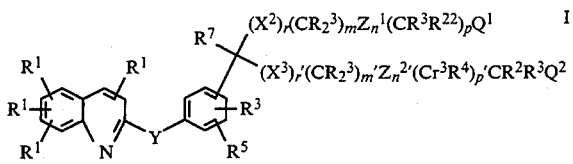

wherein:

R$^1$ is H, halogen, —CF₃, —CN, —NO₂, or N₃;

R$^2$ is lower alkyl, lower alkenyl, lower alkynyl, —F₃, —CH₂F, —CHF₂, —CH₂CF₃, substituted or unsubstituted phenyl, substituted or unsubstituted benzyl, substituted or unsubstituted 2-phenethyl, or two R$^2$ groups joined to the same carbon may form a ring of up to 8 members containing 0-2 heteroatoms chosen from O, S, and N;

R$^3$ is H or R$^2$;

R$^4$ is halogen, —NO₂, —CN, —OR$^3$, —SR$^3$, NR$^3$R$^3$, NR$^3$C(O)R$^7$ or R$^3$;

R$^5$ is H, halogen, —NO₂, —N₃, —CN, —SR$^2$, —NR$^3$R$^3$, —OR$^3$, lower alkyl, or —C(O)R$^3$;

R$^6$ is —(CH₂)$_s$—C(R$^7$R$^7$)—(CH₂)$_s$—R$^8$ or —CH₂-C(O)NR$^{12}$R$^{12}$;

R$^7$ is H or C₁-C₄ alkyl;

R$^8$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or B) the radical W-R$^9$;

R$^9$ contains up to 20 carbon atoms and is (1) an alkyl group or (2) an alkylcarbonyl group of an organic acyclic or monocyclic carboxylic acid containing not more than 1 heteroatom in the ring;

R$^{10}$ is —SR$^{11}$, —OR$^{12}$, or —NR$^{12}$R$^{12}$;

R$^{11}$ is lower alkyl, —C(O)R$^{14}$, unsubstituted phenyl, or unsubstituted benzyl;

R$^{12}$ is H, R$^{11}$, or two R$^{12}$ groups joined to the same N may form a ring of 5 or 6 members containing 1-2 heteroatoms chosen from O, S, and N;

R$^{13}$ is lower alkyl, lower alkenyl, lower alkynyl, —CF₃, or substituted or unsubstituted phenyl, benzyl, or 2-phenethyl;

R$^{14}$ is H or R$^{13}$;

R$^{15}$ is R$^3$ or halogen;

R$^{16}$ is H, C₁-C₄ alkyl, or OH;

R$^{17}$ is lower alkyl, lower alkenyl, lower alkynyl, or substituted or unsubstituted phenyl, benzyl, or 2-phenethyl;

R$^{18}$ is lower alkyl, lower alkenyl, lower alkynyl, —CF₃, or substituted or unsubstituted phenyl, benzyl, or 2-phenethyl;

R$^{19}$ is lower alkyl, lower alkenyl, lower alkynyl, —CF₃, or substituted or unsubstituted phenyl, benzyl, or 2-phenethyl;

R$^{20}$ is H, C₁-C₄ alkyl, substituted or unsubstituted phenyl, benzyl, phenethyl, or pyridinyl or two R$^{20}$ groups joined to the same N may form a saturated ring of 5 or 6 members containing 1-2 heteroatoms chosen from O, S, and N;

$R^{21}$ is H or $R^{17}$;
$R^{22}$ is $R^4$, $CHR^7OR^3$, or $CHR^7SR^2$;
m and m' are independently 0–8;
n and n' are independently 0 or 1,
p and p' are independently 0–8;
m+n+p is 1–10 when r is 1 and $X^2$ is O, S, S(O), or $S(O)_2$;
m+n+p is 0–10 when r is 1 and $X^2$ is $CR^3R^{16}$;
m+n+p is 0–10 when r is 0;
m'+n'+p' is 0–10;
r and r' are independently 0 or 1;
s is 0–3;
$Q^1$ is $-C(O)OR^3$, 1H(or 2H)-tetrazol-5-yl, $-C(O)OR^6$, $-C(O)NHS(O)_2R^{13}$, $-CN$, $-C(O)NR^{12}R^{12}$, $-NR^{21}S(O)_2R^{13}$, $-NR^{12}C(O)NR^{12}R^{12}$, $-NR^{21}C(O)R^{28}$, $-OC(O)NR^{12}R^{12}$, $-C(O)R^{19}$, $-S(O)R^{18}$, $-S(O)_2R^{18}$, $-S(O)_2NR^{12}R^{12}$, $-NO_2$, $-NR^{21}C(O)OR^{17}$, $-C(NR^{12}R^{12})=NR^{12}$, $-C(R^{13})=NOH$; or if $Q^1$ is $-C(O)OH$ and $R^{22}$ is $-OH$, $-SH$, $-CHR^7OH$ or $-NHR^3$, then $Q^1$ and $R^{22}$ and the carbons through which they are attached may form a heterocyclic ring by loss of water;
$Q^2$ is OH or $NR^{20}R^{20}$;
W is O, S, or $NR^3$;
$X^2$ and $X^3$ are independently O, S, S(O), $S(O)_2$, or $CR^3R^{16}$ with the proviso that at least one is S or $S(O)_2$;
Y is $$-CR^3R^3-CR^3R^3-,$$

or

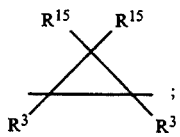

$Z^1$ and $Z^2$ are independently $-HET(-R^3-R^5)-$;
HET is the diradical of a benzene, a pyridine, a furan, or a thiophene; and the pharmaceutically acceptable salts thereof.

2. A compound of claim 1 wherein:
$R^1$ is H, halogen, $CF_3$, or $-CN$;
$R^2$ is $C_1$-$C_4$ alkyl, $-CF_3$, $-CHF_2$, $-CH_2F$, or two $R^2$ groups joined to the same carbon may form a ring of up to 6 carbons;
$R^3$ is H or $R^2$;
$CR^3R^{22}$ may be the radical of a standard amino acid;
$R^4$ is $-OR^3$, $-SR^3$, $NR^3R^3$, $NHC(O)CH_3$, or $R^3$;
$R^5$ is H or halogen;
$R^6$ is $-(CH_2)_s-C(R^7R^7)-(CH_2)_s-R^8$ or $-CH_2C(O)NR^{12}R^{12}$;
$R^7$ is H or $C_1$-$C_4$ alkyl;
$R^8$ is A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or
B) the radical $W-R^9$;
$R^9$ contains up to 20 carbon atoms and is (1) an alkyl group or (2) an alkylcarbonyl group;
$R^{10}$ is $-SR^{11}$, $-OR^{12}$, or $-NR^{12}R^{12}$;
$R^{11}$ is lower alkyl, $-C(O)R^{14}$, unsubstituted phenyl, or unsubstituted benzyl;
$R^{12}$ is H, $R^{11}$, or two $R^{12}$ groups joined to the same N may form a ring of 5 or 6 members containing 1–2 heteroatoms chosen from O, S, and N;
$R^{13}$ is lower alkyl, $-CF_3$, or substituted or unsubstituted phenyl, benzyl, or 2-phenethyl;
$R^{14}$ is H or $R^{13}$;
$R^{15}$ is $R^3$ or halogen;
$R^{16}$ is H, $C_1$-$C_4$ alkyl, or OH;
$R^{22}$ is $R^4$, $-CH_2OR^3$, or $-CH_2SR^2$;
m and m' are independently 0–4;
n and n' are independently 0 or 1;
p and p' are independently 0–4;
m+n+p is 1–9 when r is 1 and $X^2$ is O or S;
m+n+p is 0–9 when r is 1 and $X^2$ is $CR^3R^{16}$;
m+n+p is 0–9 when r is 0;
m'+n'+p' is 1–9;
r and r' are independently 0 or 1;
s is 0–3;
$Q^1$ is $-C(O)OR^3$, 1H(or 2H)-tetrazol-5-yl, $-C(O)OR^6$, $-C(O)NHS(O)_2R^{13}$, $-C(O)NR^{12}R^{12}$, $-NHS(O)_2R^{13}$; or if $Q^1$ is C(O)OH and $R^{22}$ is $-OH$, $-SH$, $-CH_2OH$ or $-NHR^3$ then $Q^1$ and $R^{22}$ and the carbons through which they are attached may form a heterocyclic ring by loss of water;
$Q^2$ is OH;
W is O, S, or NH;
$X^2$ and $X^3$ are independently O, S, or $CR^3R^{16}$;
Y is

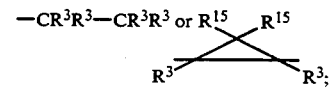

$Z^1$ and $Z^2$ are independently $-HET(-R^3-R^5)-$;
HET is the diradical of a benzene, pyridine, furan, or thiophene; and the pharmaceutically acceptable salts thereof.

3. A compound of claim 1 wherein the $R^{22}\alpha$ to $Q^1$ is lower alkyl, $CF_3$ or substituted or unsubstituted phenyl.

4. A compound of claim 1 of the Formula Ia:

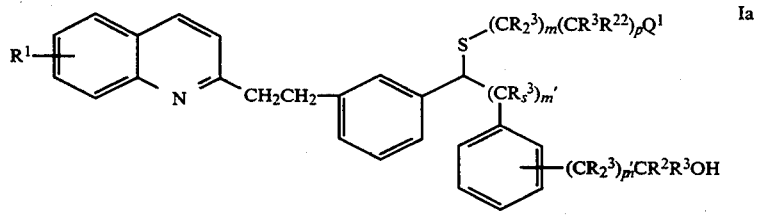

wherein:
$R^1$ is H, halogen, CN, or $CF_3$;
Rhu 22 is $R^3$, $-CH_2OR^3$, or $-CH_2SR^2$;
$Q^1$ is $-C(O)OH$, 1H(or 2H)-tetrazol-5-yl, $-C(O)NHS(O)_2R^{13}$, $-C(O)NR^{12}R^{12}$, or $-NHS(O)_2R^{13}$;

m' is 2 or 3;
p' is 0 or 1;
m+p is 1–5; and the pharmaceutically acceptable salts thereof.

5. A compound of claim 4 wherein m is 0.
6. A compound of claim 4 wherein the carbon α to $Q^1$ is lower alkyl-substituted.
7. A compound of claim 1 of the Formula Ib:

m is 0, 2, or 3;
p is 0 or 1;
p' is 1–4;
m+p is 0–4; and the pharmaceutically acceptable salts thereof.

8. A compound of claim 1 of Formula I'

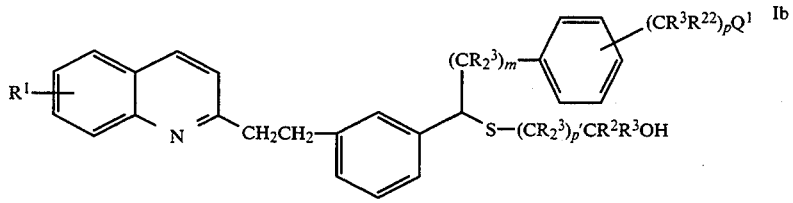

wherein:
$R^1$ is H, halogen, CN, or $CF_3$;
$R^{22}$ is $R^3$, $-CH_2OR^3$, or $-CH_2SR^2$;
$Q^1$ is $-C(O)OH$, 1H(or 2H)-tetrazol-5-yl, $-C(O)NHS(O)_2R^{13}$, $-C(O)NR^{12}R^{12}$, or $-NHS(O)_2R^{13}$;

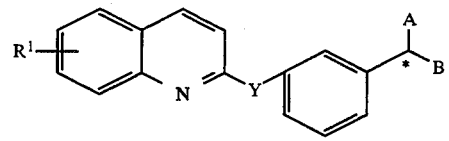

wherein the substituents are as follows:

| | * | $R^1$ | Y | A | B |
|---|---|---|---|---|---|
| 1 | RS | 7-Cl | CHCH$_2$CH | SCH$_2$CHMeCO$_2$H | (CH$_2$)$_2$(1,2-phe)CMe$_2$OH |
| 2 | RS | 7-Cl | CH$_2$CH$_2$ | SCH$_2$CHMeCO$_2$H | (CH$_2$)$_2$(1,2-phe)(1-c-Bu)OH |
| 3 | RS | 7-Cl | CH$_2$CH$_2$CH | SCH$_2$CHEtCO$_2$H | (CH$_2$)$_2$(4-Cl-1,2-phe)CMe$_2$OH |
| 4 | RS | 7-Cl | CH$_2$CH$_2$ | SCH$_2$CHMeCO$_2$H | (1,3-phe)C$_2$OH |
| 5 | RS | 7-Cl | CHCH$_2$CH | S(CH$_2$)$_2$CMe$_2$OH | (CH$_2$)$_2$(1,2-phe)CO$_2$H |
| 6 | S | 7-Cl | CH$_2$CH$_2$ | SCH$_2$(S)CHEtCO$_2$H | (CH$_2$)$_2$(1,2-phe)CMe$_2$OH |
| 7 | S | 7-Cl | CH$_2$CH$_2$ | SCH$_2$(R)CH(NH$_2$)Co$_2$H | (CH$_2$)$_2$(1,2-phe)CMe$_2$OH |
| 8 | S | 7-Cl | CH$_2$CH$_2$ | SCH$_2$(S)CHMeCO$_2$H | (CH$_2$)$_2$(1,2-phe)CMe$_2$OH |
| 9 | S | 7-Cl | CH$_2$CH2 | SCH$_2$(S)CH(n-Pr)CO$_2$H | (CH$_2$)$_2$(1,2-phe)CMe$_2$OH |
| 10 | RS | 7-Cl | CH$_2$CH$_2$CH | SCH$_2$CHEtCO$_2$H | (CH$_2$)$_2$(1,2-phe)CMe$_2$OH |
| 11 | RS | 7-Cl | CHCBr$_2$CH | SCH$_2$CHEtCO$_2$H | (CH$_2$)$_2$(1,2-phe)CMe$_2$OH |
| 12 | RS | 7-Cl | CH$_2$CH$_2$ | SCH$_2$CMe$_2$CO$_2$H | (CH$_2$)$_2$(1,2-phe)CMe$_2$OH |
| 13 | RS | 7-Cl | CH$_2$CH$_2$ | SCH$_2$CHMeCO$_2$H | (CH$_2$)$_2$(1,2-phe)CMe$_2$OH |
| 14 | RS | 7-Cl | CH$_2$CH$_2$ | S(CH$_2$)$_2$CO$_2$H | (CH$_2$)$_2$(1,2-phe)CMe$_2$OH |
| 15 | RS | 7-Br | CH$_2$CH$_2$ | SCH$_2$CHMeCO$_2$H | (CH$_2$)$_2$(1,2-phe)CMe$_2$OH |
| 16 | RS | 7-Cl | CH$_2$CH$_2$ | S(CH$_2$)CMe$_2$OH | (CH$_2$)$_2$(1,2-phe)CHMeCO$_2$H |
| 17 | RS | 7-Cl | CH$_2$CH$_2$ | SCH$_2$CHEtCO$_2$H | S(CH$_2$)$_2$CMe$_2$OH |
| 18 | S | 7-Cl | CH$_2$CH$_2$ | SCH$_2$CHMeCO$_2$H | (CH$_2$)$_2$(1,2-phe)C(CF$_3$)$_2$OH |
| 19 | RS | 7-Cl | CHCH$_2$CH | SCH$_2$CHEtCO$_2$H | (CH$_2$)$_2$(1,3-phe)CMe$_2$OH |
| 20 | RS | 7-Cl | CHCH$_2$CH | SCH$_2$CHEtCO$_2$H | SCH$_2$CMe$_2$CMe$_2$OH |
| 21 | RS | 7-Cl | CH$_2$CH$_2$ | S(CH$_2$)$_2$CMe$_2$OH | (CH$_2$)$_2$(1,2-phe)CO$_2$H |
| 22 | RS | 7-Cl | CH$_2$CH$_2$ | S(CH$_2$)$_2$CMe$_2$OH | (CH$_2$)$_2$(1,2-phe)CONH$_2$ |
| 23 | RS | 7-Cl | CH$_2$CH$_2$ | SCH$_2$CHMeCO$_2$H | SCH$_2$(1,2-phe)CMe$_2$OH |
| 24 | RS | 7-CF$_3$ | CH$_2$CH$_2$ | SCH$_2$CHMeCO$_2$H | (CH$_2$)$_2$(1,4-phe)CMe$_2$OH |
| 25 | RS | 7-Cl | CH$_2$CH$_2$ | SCH$_2$CH(OMe)CO$_2$H | (CH$_2$)$_2$(1,2-phe)CMe$_2$OH |
| 26 | RS | 7-Cl | CHCH$_2$CH | SCH$_2$CHEtCO$_2$H | (CH$_2$)$_2$(1,2-phe)CH(CF$_3$)OH |
| 27 | RS | H | CHCH$_2$CH | SCH$_2$CHMeCO$_2$H | (CH$_2$)$_2$(1,2-phe)CMe$_2$OH |
| 28 | RS | H | CH$_2$CH$_2$ | SCH$_2$CHEtCO$_2$H | (CH$_2$)$_2$(1,2-phe)CMe$_2$OH |
| 29 | RS | 7-Br | CH$_2$CH$_2$ | SCH$_2$CHEtCO$_2$H | (CH$_2$)$_2$(4-Br-1,2-phe)CMe$_2$OH |
| 30 | RS | 7-CN | CH$_2$CH$_2$ | SCH$_2$CHEtCO$_2$H | (CH$_2$)$_2$(1,2-phe)CMeEtOH |
| 31 | RS | 7-Br | CHCH$_2$CH | SCH$_2$CHEtCO$_2$H | (CH$_2$)$_2$(1,2-phe)CEt$_2$OH |
| 32 | RS | 7-Cl | CH$_2$CH$_2$ | SCH$_2$CHMeCO$_2$H | (CH$_2$)$_2$(1,2-phe)CMe$_2$NH$_2$ |
| 33 | RS | 7-Cl | CHCH$_2$CH | SCH$_2$CHEtCO$_2$H | (CH$_2$)$_2$(1,2-phe)CHMeNHMe |
| 34 | RS | 7-Br | CH$_2$CH$_2$ | SCH$_2$CHEtCO$_2$H | (CH$_2$)$_2$(1,2-phe)CHMeNMe$_2$ |
| 35 | RS | 7-Cl | CH$_2$CH$_2$ | SCH$_2$CHEtCO$_2$H | (CH$_2$)$_2$(2,5-fur)CMe$_2$OH |
| 36 | RS | 7-Cl | CH$_2$CH$_2$ | SCH$_2$CHEtCO$_2$H | (CH$_2$)$_2$(2,6-pye)CMe$_2$OH |
| 37 | RS | 7-Cl | CH$_2$CH$_2$ | SCH$_2$CHEtCO$_2$H | (CH$_2$)$_2$(4,2-pye)CMe$_2$OH |
| 38 | RS | 7-Cl | CHCH$_2$CH | SCH$_2$CHEtCO$_2$H | (2,5-thio)CMe$_2$OH |
| 39 | RS | 7-Cl | CH$_2$CH$_2$ | SCH$_2$CHEtCO$_2$H | (3,2-pye)CMe$_2$OH |
| 40 | RS | 7-Br | CH$_2$CH$_2$ | SCH$_2$CHEtCO$_2$H | (1,4-phe)CMe$_2$OH |
| 41 | RS | 7-Cl | CH$_2$CH$_2$ | SCH$_2$CHMeCONHS(O)$_2$Me | (CH$_2$)$_2$(1,2-phe)CMe$_2$OH |
| 42 | RS | 7-Cl | CH$_2$CH$_2$ | SCH$_2$CHMeCONH$_2$ | (CH$_2$)$_2$(1,2-phe)CMe$_2$OH |
| 43 | RS | 7-Cl | CH$_2$CH$_2$ | SCH$_2$CHMeTz | (CH$_2$)$_2$(1,2-phe)CMe$_2$OH |
| 44 | RS | 7-Cl | CHCH$_2$CH | SCH$_2$CHEtTz | (CH$_2$)$_2$(1,2-phe)CMe$_2$OH |
| 45 | RS | 7-Cl | CHCH$_2$CH | SCH$_2$CHEtCONHS(O)$_2$CF$_3$ | (CH$_2$)$_2$(1,2-phe)CMe$_2$OH |
| 46 | RS | 7-Cl | CH$_2$CH$_2$ | SCH$_2$CHMeNO$_2$ | (CH$_2$)$_2$(1,2-phe)CMe$_2$OH |
| 47 | RS | 7-Cl | CH$_2$CH$_2$ | S(CH$_2$)$_2$CONHS(O)$_2$Ph | (CH$_2$)$_2$(1,2-phe)CMe$_2$OH |
| 48 | RS | 7-Cl | CH$_2$CH$_2$ | SCH$_2$CHEtCO$_2$H | (CH$_2$)$_2$(1,2-phe)CH$_2$CMe$_2$OH |
| 49 | RS | 7-Cl | CHCH$_2$CH | SCH$_2$CHEtCO$_2$H | (CH$_2$)$_3$(1,2-phe)CMe$_2$OH |
| 50 | S | 7-Cl | CH$_2$CH$_2$ | SCH$_2$CH(CH$_2$CH=CH$_2$)CO$_2$H | (CH$_2$)$_2$(1,2-phe)CMe$_2$OH |

-continued

|  | * | R¹ | Y | A | B |
|---|---|---|---|---|---|
| 51 | S | 7-Cl | CHCH₂CH | SCH₂CHEtCO₂H | (CH₂)₂(1,2-phe)CHMeOH |
| 52 | S | 7-Cl | CH₂CH₂ | SCH₂CH(CH₂SMe)CO₂H | (CH₂)₂(1,2-Phe)CMe₂OH |
| 53 | S | 7-Cl | CHCH₂CH | SCH₂CH(c-Pr)CO₂H | (CH₂)₂(1,2-phe)CMe₂OH |
| 54 | S | 7-Cl | CH₂CH₂ | SCH₂CH(CH₂C≡CH)CO₂H | (CH₂)₂(1,2-phe)CMe₂OH |
| 55 | S | 7-Cl | CH₂CH₂ | SCH₂CHPhCO₂H | (CH₂)₂(1,2-phe)CMe₂OH |
| 56 | RS | 7-Cl | CH₂CH₂ | SCH₂CHEtCO₂H | (1,2-phe)CMe₂OH |
| 57 | RS | 7-Cl | CH₂CH₂ | S(CH₂)₂CMe₂OH | (1,3-phe)CO₂H |
| 58 | RS | 7-Cl | CH₂CH₂ | S(CH₂)₂CO₂H | CH₂CHOH(1,3-phe)CN₄H |
| 59 | RS | 7-Cl | CH₂CH₂ | S(CH₂)₂CO₂H | CH₂CHOH(1,4-phe)CN₄H |
| 60 | S | 7-Cl | CH₂CH₂ | S(CH₂)₂CO₂H | (CH₂)₂(1,2-phe)CMe₂OH |
| 61 | S | 7-Cl | CH₂CH₂ | SCH₂CHCF₃CO₂H | (CH₂)₂(1,2-phe)CMe₂OH |
| 62 | S | 7-Cl | CH₂CH₂ | S(CH₂)₃CO₂H | (CH₂)₂(1,2-phe)CMe₂OH |
| 63 | S | 7-Cl | CH₂CH₂ | S(CH₂)₂CHMeCO₂H | (CH₂)₂(1,2-phe)CMe₂OH |
| 64 | S | 7-Cl | CH₂CH₂ | S(O)₂CH₂(S)CHEtCO₂H | (CH₂)₂(1,2-phe)CMe₂OH |
| 65 | S | 7-Cl | CH₂CH₂ | SCH₂CH(CH₂OMe)CO₂H | (CH₂)₂(1,2-phe)CMe₂OH |
| 66 | S | 7-Cl | CH₂CH₂ | S(CH₂)₂CMe₂OH | (CH₂)₂(1,2-phe)CO₂H |
| 67 | R | 7-Cl | CH₂CH₂ | S(CH₂)₂CMe₂OH | (CH₂)₂(1,2-phe)CO₂H |
| 68 | S | 7-Cl | CH₂CH₂ | SCH₂(S)CHEtCO₂H | (CH₂)₂(1,3-phe)CMe₂OH |
| 69 | S | 7-Cl | CH₂CH₂ | SCH₂CHEtCO₂H | (CH₂)₂(1,3-phe)(1,1-c-Bu)OH |
| 70 | S | 7-Cl | CH₂CH₂ | S(CH₂)₂CMe₂OH | (CH₂)₃(1,2-phe)COOH |
| 71 | R | 7-Cl | CH₂CH₂ | S(CH₂)₂CO₂H | S(CH₂)₂(1,-c-Pen)OH |
| 72 | S | 7-Cl | CH₂CH₂ | SCH₂CH(CH₂CF₃)CO₂H | (CH₂)₂(1,2-phe)CMe₂OH |
| 73 | S | 7-Cl | CH₂CH₂ | S(CH₂)₂CMe₂OH | (CH₂)₂(4-Cl-1,2-phe)CO₂H |
| 74 | R | 7-Cl | CH₂CH₂ | SCH₂(S)CHEtCONHS(O)₂Me | (CH₂)₂(1,2-phe)CMe₂OH |
| 75 | S | 7-Cl | CH₂CH₂ | S(CH₂)₂CMeOH | (CH₂)₂(1,3-phe)CMe₂CO₂H |
| 76 | S | 7-Cl | CH₂CH₂ | S(CH₂)₂CMeOH | (CH₂)₂(1,3-phe)CHMeCO₂H |
| 77 | S | 7-Cl | CH₂CH₂ | S(CH₂)₃CMe₂OH | (CH₂)₂(1,2-Phe)CO₂H |
| 78 | S | 7-Cl | CH₂CH₂ | SCH₂(S)CHEtCO₂H | (CH₂)₂(1,4-phe)CMe₂OH |
| 79 | RS | 7-Cl | CH₂CH₂ | S(CH₂)₂CMe₂OH | (CH₂)₂(1,3-phe)CN₄H |
| 80 | S | 7-Cl | CH₂CH₂ | S(CH₂)₃CMe₂OH | (CH₂)₂(1,2-phe)CHMeCO₂H |
| 81 | S | 7-Cl | CH₂CH₂ | S(CH₂)₃CMe₂OH | (CH₂)₂(1,2-phe)CHMeCONHS(O)₂CH₃ |
| 82 | S | 7-Cl | CH₂CH₂ | S(CH₂)₂CMe₂OH | (CH₂)₃(1,2-phe)CO₂H |
| 83 | R | 7-Cl | CH₂CH₂ | S(O)₂CH₂(S)CHEtCO₂H | (CH₂)₂(1,2-phe)CMe₂OH |
| 84 | S | 7-Cl | CH₂CH₂ | S(CH₂)₂CMe₂OH | (CH₂)₂(4-Cl-1,2-phe)CHMeCO₂H |
| 85 | S | 7-Cl | CH₂CH₂ | SCH₂(S)CHMeCO₂H | (CH₂)₂(1,2-phe)CH₂CMe₂OH |
| 86 | S | 7-Cl | CH₂CH₂ | S(CH₂)₂CME₂OH | (CH₂)₂(1,2-phe)CO₂Me |
| 87 | S | 7-Cl | CH₂CH₂ | S(CH₂)₃CMe₂OH | (CH₂)₂(4-Cl-1,2-phe)CO₂H |
| 88 | R | 7-Cl | CH₂CH₂ | S(CH₂)₂CMe₂OH | (CH₂)₂(4-Cl-1,2-phe)CO₂H |
| 89 | S | 7-Cl | CH₂CH₂ | S(CH₂)₃CMe₂OH | (CH₂)₂(1,2-phe)CMe₂CO₂H |
| 90 | S | 7-Cl | CH₂CH₂ | S(CH₂)₂CMe₂OH | (CH₂)₃(R)CHMe₂CO₂H |
| 91 | S | 7-Cl | CH₂CH₂ | S(CH₂)₃CEt₂OH | (CH₂)₂(1,2-phe)CO₂H |
| 92 | S | 7-Cl | CH₂CH₂ | S(CH₂)₃CEt₂OH | (CH₂)₂(1,2-phe)CHMeCO₂H |
| 93 | R | 7-Cl | CH₂CH₂ | SCHMeCH₂CO₂H | (CH₂)₂(1,2-phe)CMe₂OH |
| 94 | S | 7-Cl | CH₂CH₂ | S(CH₂)₃CMe₂OH | (CH₂)₂(1,2-phe)CHEtCO₂H |
| 95 | S | 7-Cl | CH₂CH₂ | S(CH₂)₃CMe₂OH | (CH₂)₂(1,2-phe)CH(n-Pr)CO₂H |
| 96 | S | 7-Cl | CH₂CH₂ | S(CH₂)₃CMe₂OH | (CH₂)₂(1,2-phe)CH(i-Pr)CO₂H |
| 97 | R | 7-Cl | CH₂CH₂ | SCH₂MeCHMeCO₂H | (CH₂)₂(1,2-phe)CMe₂OH |
| 98 | R | 7-Cl | CH₂CH₂ | S(CH₂)₂CMe₂OH | (CH₂)₃(R)CHMeCO₂H |
| 99 | R | 7-Cl | CH₂CH₂ | SCH₂(S)CHMeCN₄H | (CH₂)₂(1,2-phe)CMe₂OH |
| 100 | S | 7-Cl | CH₂CH₂ | SCH₂(S)CHMeCO₂H | (CH₂)₂(3-OH-1,4-phe)CHMeOH |
| 101 | S | 7-Cl | CH₂CH₂ | S(CH₂)₃CHMeOH | (CH₂)₂(1,2-phe)CHMeCO₂H |
| 102 | R | 7-Cl | CH₂CH₂ | S(S)CHMeCH₂CO₂H | (CH₂)₂(1,2-phe)CMe₂OH |
| 103 | R | 7-Cl | CH₂CH₂ | S(R)CHMeCH₂CO₂H | (CH₂)₂(1,2-phe)CMe₂OH |
| 104 | R | 7-Cl | CH₂CH₂ | S(S)CHMe(S)CHMeCO₂H | (CH₂)₂(1,2-phe)CMe₂OH |
| 105 | R | 7-Cl | CH₂CH₂ | S(R)CHMe(R)CHMeCO₂H | (CH₂)₂(1,2-phe)CMe₂OH |
| 106 | R | 7-Cl | CH₂CH₂ | SCHEtCH₂CO₂H | (CH₂)₂(1,2-phe)CMe₂OH |
| 107 | S | 7-Cl | CH₂CH₂ | S(CH₂)₃CHMeOH | (CH₂)₂(1,2-phe)CHEtCO₂H |
| 108 | S | 7-Cl | CH₂CH₂ | SCH₂(S)CHMeCO₂H | (CH₂)₂(1,2-phe)CH(OH)CH₂(OH)Ph |
| 109 | R | 7-Cl | CH₂CH₂ | SCMe₂CH₂CO₂H | (CH₂)₂(1,2-phe)CMe₂OH |
| 110 | R | 7-Cl | CH₂CH₂ | SCH₂CHMeCH₂CO₂H | (CH₂)₂(1,2-phe)CMe₂OH |
| 111 | R | 7-Cl | CH₂CMe₂ | SCH₂(1,1-c-Pr)CH₂CO₂H | (CH₂)₂(1,2-phe)CMe₂OH |
| 112 | S | 7-Cl | CMe₂CH₂ | SCH₂(1,1-c-Pr)CH₂CO₂H | (CH₂)₂(1,2-phe)CO₂H |
| 113 | S | 7-Cl | Me₂H₂CH₂ | S(CH₂)₃CMe₂OH | (CH₂)₂(1,2-phe)(R)CHEtCO₂H |
| 114 | S | 7-Cl | CH₂CH₂ | S(CH₂)₃CMe₂OH | (CH₂)₂(1,2-phe)(S)CHEtCO₂H |
| 115 | S | 7-Cl | CH₂CH₂ | S(CH₂)₃CMe₂OH | (CH₂)₂(4-Cl-1,2-phe)CHEtCO₂H |
| 116 | S | 7-Cl | CH₂CH₂ | S(CH₂)₃CMe₂OH | (CH₂)₂(1,2-phe)CEt₂CO₂H |
| 117 | S | 7-Cl | CH₂CH₂ | S(CH₂)₃CMe₂OH | (CH₂)₂(1,2-phe)CH₂CO₂H |
| 118 | S | 7-Cl | CH₂CH₂ | S(CH₂)₃CMe₂OH | (CH₂)₂(1,2-phe)CH(OH)CO₂H |
| 119 | S | 7-Cl | CHMeCHMe | SCH₂(1,1-c-Pr)CH₂CO₂H | (CH₂)₂(1,2-phe)CHEtCO₂H |
| 120 | S | 7-Cl | CH₂CH₂ | S(CH₂)₃CMe₂OH | (CH₂)₂CHMeCH₂CO₂H |
| 121 | R | 7-Cl | CH₂CH₂ | SCH₂CMe₂CH₂CO₂H | (CH₂)₂(1,2-phe)CMe₂OH |
| 122 | R | 7-Cl | CH₂CH₂ | S(CH₂)₄CMe₂OH | (CH₂)₂(1,2-phe)CHEtCO₂H |
| 123 | S | 7-F | CH₂CH₂ | SCH₂CMe₂CH₂CO₂H | (CH₂)₂(1,2-phe)CO₂H |
| 124 | S | 7-Br | CH₂CH₂ | SCH₂CMe₂CH₂CO₂H | (CH₂)₂(1,2-phe)CO₂H |
| 125 | S | 7-I | CH₂CH₂ | SCH₂(1,1-c-Pr)CH₂CO₂H | (CH₂)₂(1,2-phe)CMe₂OH |
| 126 | S | 7-CF₃ | CH₂CH₂ | SCH₂CMe₂CH₂CO₂H | (CH₂)₂(1,2-phe)CHMeCO₂H |
| 127 | S | 7-CN | CH₂CH₂ | SCH₂CMe₂CH₂CO₂H | (CH₂)₂(1,2-phe)CHEtCO₂H |
| 128 | S | 7-NO₂ | CH₂CH₂ | SCH₂(1,1-c-Pr)CH₂CO₂H | (CH₂)₂(1,2-phe)CMe₂OH |
| 129 | R | 7-N₃ | CH₂CH₂ | SCH₂(1,1-c-Pr)CH₂CO₂H | (CH₂)₂(1,2-phe)CMe₂OH |
| 130 | RS | 7-Cl | CH₂CH₂ | S(CH₂)₂CMe₂OH | (CH₂)₂CMe₂CH₂CO₂H |
| 131 | R | 7-Cl | CH₂CH₂ | S(1,2-phe)CH₂CO₂H | (CH₂)₂(1,2-phe)CMe₂OH |

-continued

| | * | R¹ | Y | A | B |
|---|---|---|---|---|---|
| 132 | R | 7-Cl | CH$_2$CH$_2$ | S(CH$_2$)$_3$CMe$_2$OH | (CH$_2$)$_2$(1,2-phe)CHEtCO$_2$H |
| 133 | S | 7-Cl | CH$_2$CH$_2$ | S(CH$_2$)$_2$CMe$_2$OH | (CH$_2$)$_2$(1,2-phe)CHEtCO$_2$H |
| 134 | S | 7-Cl | CH$_2$CH$_2$ | S(CH$_2$)$_3$CMe(4-Cl-Ph)OH | (CH$_2$)$_2$(1,2-phe)CHEtCO$_2$H |
| 135 | R | 7-Cl | CH$_2$CH$_2$ | SCH$_2$(1,2-phe)CMe$_2$OH | (CH$_2$)$_2$CMe$_2$CH$_2$CO$_2$H |
| 136 | R | 7-Cl | CH$_2$CH$_2$ | SCH$_2$(1,1-c-Pr)CH$_2$CO$_2$H | (CH$_2$)$_2$(1,2-phe)CMe$_2$OH |
| 137 | R | 7-Cl | CH$_2$CH$_2$ | SCH$_2$(1,1-c-Bu)CH$_2$CO$_2$H | (CH$_2$)$_2$(1,2-phe)CMe$_2$OH |
| 138 | R | 7-Cl | CH$_2$CH$_2$ | SCH$_2$CMe$_2$CHMeCO$_2$H | (CH$_2$)$_2$1,2-phe)CMe$_2$OH |
| 139 | S | 7-Cl | CH$_2$CH$_2$ | SCH$_2$(1,2-phe)CMe$_2$OH | (CH$_2$)$_2$CMe$_2$CH$_2$CO$_2$H |
| 140 | R | 7-Cl | CH$_2$CH$_2$ | SCHMeCMe$_2$CH$_2$CO$_2$H | (CH$_2$)$_2$(1,2-phe)CMe$_2$OH |
| 141 | R | 7-Cl | CH$_2$CH$_2$ | S(1,1-c-Pr)CH$_2$CO$_2$H | (CH$_2$)$_2$(1,2-phe)CMe$_2$OH |
| 142 | R | 7-Cl | CH$_2$CH$_2$ | S(1,1-c-Pr)CHMeCO$_2$H | (CH$_2$)$_2$(1,2-phe)CMe$_2$OH |
| 143 | R | 7-Cl | CH$_2$CH$_2$ | S(1,1-c-Pr)CH$_2$CO$_2$H | (CH$_2$)$_2$(1,3-phe)CMe$_2$OH |
| 144 | R | 7-Cl | CH$_2$CH$_2$ | S(1,1-c-Pr)CH$_2$CO$_2$H | (CH$_2$)$_2$(1,2-phe)(1,1-c-Bu)OH |
| 145 | R | 7-Cl | CH$_2$CH$_2$ | S(1,1-c-Pr)CH$_2$CO$_2$H | (CH$_2$)$_2$(1,3-phe)(1,1-c-Bu)OH |
| 146 | R | 7-Cl | CH$_2$CH$_2$ | SCH$_2$(1,1-c-Pr)CH$_2$CO$_2$H | (CH$_2$)$_2$(1,3-phe)CMe$_2$OH |
| 147 | R | 7-Cl | CHCH$_2$CH | SCH$_2$(1,1-c-Pr)CH$_2$CO$_2$H | (CH$_2$)$_2$(1,2-phe)CMe$_2$OH |
| 148 | R | 7-Cl | CHCH$_2$CH | S(1,1-c-Pr)CH$_2$CO$_2$H | (CH$_2$)$_2$(1,2-phe)CMe$_2$OH |
| 149 | R | 7-Cl | CHCH$_2$CH | SCMe$_2$CH$_2$CO$_2$H | (CH$_2$)$_2$(1,2-phe)CMe$_2$OH |
| 150 | R | 7-Cl | CHCH$_2$CH | S(1,1-c-Pr)(S)CHMeCO$_2$H | (CH$_2$)$_2$(1,2-phe)CMe$_2$OH |
| 151 | R | 7-Cl | CHCH$_2$CH | S(1,1-c-Pr)CHMeCO$_2$H | (CH$_2$)$_2$(1,3-phe)CMe$_2$OH |
| 152 | R | 7-Cl | CHCH$_2$CH | S(1,1-c-Pr)CH$_2$CO$_2$H | (CH$_2$)$_2$(1,2-phe)(1,1-c-Bu)OH |
| 153 | R | 7-Cl | CHCH$_2$CH | S(1,1-c-Pr)CH$_2$CO$_2$H | (CH$_2$)$_2$(1,3-phe)(1,1-c-Bu)OH |
| 154 | S | 7-Cl | CH$_2$CH$_2$ | SCH$_2$CHEtCO$_2$H | (CH$_2$)$_2$(1,2-phe)CMe$_2$OH |
| 155 | S | 7-Cl | CH$_2$CH$_2$ | SCH$_2$(1,2-phe)CMe$_2$OH | CH$_2$)$_2$(1,2-phe)CHEtCO$_2$H |
| 156 | S | 7-Cl | CH$_2$CH$_2$ | S(CH$_2$)$_2$CMe$_2$OH | (CH$_2$)$_2$(1,2-phe)CH$_2$CO$_2$H |
| 157 | S | 7-Cl | CH$_2$CH$_2$ | SCH$_2$(1,2-phe)CHMe$_2$OH | (CH$_2$)$_2$(1,2-phe)CH$_2$CO$_2$H |
| 158 | S | 7-Cl | CH$_2$CH$_2$ | S(CH$_2$)$_2$CMe$_2$OH | (CH$_2$)$_2$(4-Cl-1,2-phe)CH$_2$CO$_2$H |
| 159 | S | 7-Cl | CH$_2$CH$_2$ | SCH$_2$(1,2-phe)CMe$_2$OH | (CH$_2$)$_2$(4-Cl-1,2-phe)CH$_2$CO$_2$H |
| 160 | R | 7-Cl | CH$_2$CH$_2$ | SCH$_2$CMe$_2$CH$_2$CO$_2$H | (CH$_2$)$_4$(1,2-phe)CMe$_2$OH |
| 161 | S | 7-Cl | CH$_2$CH$_2$ | S(CH$_2$)$_3$CMe$_2$OH | (CH$_2$)$_2$(4-Cl-1,2-phe)CH$_2$CO$_2$H |
| 162 | S | 7-Cl | CH$_2$CH$_2$ | SCH$_2$(1,2-phe)CMe$_2$OH | (CH$_2$)$_2$(1,1-c-Pr)CH$_2$CO$_2$H |

9. A pharmaceutical composition comprising a therapeutically effective amount of a compound of claim 1 and a pharmaceutically acceptable carrier.

10. The pharmaceutical composition of claim 9 additionally comprising an effective amount of a second active ingredient selected from the group consisting of non-steroidal anti-inflammatory drugs; peripheral analgesic agents; cyclooxygenase inhibitors; leukotriene antagonists; leukotriene bisynthesis inhibitors; H2-receptor antagonists; antihistaminic agents; prostaglandin antagonists; thromboxane antagonists; thromboxane synthetase inhibitors; and ACE antagonists.

11. A pharmaceutical composition according to claim 10, wherein the second active ingredient is a non-steroidal anti-inflammatory drug.

12. A pharmaceutical composition of claim 11, wherein the weight ratio of said compound of claim 1 to said second active ingredient ranges from about 1000:1 to 1:1000.

13. A method of preventing the synthesis, the action, or the release of SRS-A or leukotrienes in a mammal which comprises administering to said mammal an effective amount of a compound of claim 1.

14. The method of claim 13 wherein the mammal is man.

15. A method of treating asthma in a mammal comprising administering to a mammal in need of such treatment a therapeutically effective amount of a compound of claim 1.

16. A method of treating inflammatory deseases of the eye in a mammal which comprises administering to a mammal in need of such treatment a therapeutically effective amount of a compound of claim 1.

17. The method of claim 16 wherein the mammal is man.

* * * * *